(12) United States Patent
Tokuoka et al.

(10) Patent No.: US 11,147,833 B2
(45) Date of Patent: Oct. 19, 2021

(54) THERAPEUTIC AGENT FOR HYPERPHOSPHATEMIA

(71) Applicants: FUJIFILM Corporation, Tokyo (JP); Kyowa Kirin Co., Ltd., Tokyo (JP)

(72) Inventors: Shinsuke Tokuoka, Ashigarakami-gun (JP); Hayato Yoshida, Ashigarakami-gun (JP); Yuichiro Kondo, Tokyo (JP)

(73) Assignees: FUJIFILM Corporation, Tokyo (JP); Kyowa Kirin Co., Ltd., Tokyo (JP)

( * ) Notice: Subject to any disclaimer, the term of this patent is extended or adjusted under 35 U.S.C. 154(b) by 0 days.

(21) Appl. No.: 16/456,822

(22) Filed: Jun. 28, 2019

(65) Prior Publication Data

US 2019/0321392 A1 Oct. 24, 2019

Related U.S. Application Data

(63) Continuation of application No. PCT/JP2018/038465, filed on Oct. 16, 2018.

(30) Foreign Application Priority Data

Oct. 16, 2017 (JP) ............................. JP2017-200016
Dec. 28, 2017 (JP) ............................. JP2017-252895
Jun. 26, 2018 (JP) ............................. JP2018-121071

(51) Int. Cl.
*A61K 31/785* (2006.01)

(52) U.S. Cl.
CPC ................................ *A61K 31/785* (2013.01)

(58) Field of Classification Search
None
See application file for complete search history.

(56) References Cited

U.S. PATENT DOCUMENTS

| | | | |
|---|---|---|---|
| 4,605,701 A * | 8/1986 | Harada | C08F 8/00 525/107 |
| 4,799,962 A | 1/1989 | Ahmed | |
| 5,496,545 A * | 3/1996 | Holmes-Farley | A61K 31/795 424/78.11 |
| 5,496,845 A | 3/1996 | Martin et al. | |
| 6,180,754 B1 | 1/2001 | Stutts et al. | |
| 6,362,266 B1 | 3/2002 | Buchholz et al. | |
| 6,383,518 B1 | 5/2002 | Matsuda et al. | |
| 6,482,872 B2 | 11/2002 | Downie | |
| 6,525,113 B2 | 2/2003 | Klix et al. | |
| 6,565,768 B1 | 5/2003 | Dentler et al. | |
| 6,696,087 B2 | 2/2004 | Matsuda et al. | |
| 6,710,162 B2 | 3/2004 | Rea | |
| 6,733,780 B1 | 5/2004 | Tyler et al. | |
| 6,806,350 B2 | 10/2004 | Stanek et al. | |
| 7,067,614 B2 | 6/2006 | Rea | |
| 7,229,613 B2 | 6/2007 | Burke et al. | |
| 7,261,880 B2 | 8/2007 | Burke et al. | |
| 7,271,237 B2 | 9/2007 | Rea | |
| 7,275,928 B2 | 10/2007 | Kolesar et al. | |
| 7,388,056 B2 | 6/2008 | Gopalkrishna et al. | |
| 7,449,605 B2 | 11/2008 | Chang et al. | |
| 7,459,502 B2 | 12/2008 | Connor et al. | |
| 7,541,024 B2 | 6/2009 | Petersen et al. | |
| 7,592,417 B2 | 9/2009 | Rea | |
| 7,608,674 B2 | 10/2009 | Connor et al. | |
| 7,846,425 B2 | 12/2010 | Hegde et al. | |
| 7,879,972 B2 | 2/2011 | Rea | |
| 7,943,597 B2 | 5/2011 | Lewis et al. | |
| 7,964,182 B2 | 6/2011 | Omray et al. | |
| 8,187,631 B2 | 5/2012 | Tyler et al. | |
| 8,187,634 B2 | 5/2012 | Hegde et al. | |
| 8,198,399 B2 | 6/2012 | Rea | |
| 8,377,428 B2 | 2/2013 | Peterson et al. | |
| 8,378,036 B2 | 2/2013 | Rea | |
| 8,389,640 B2 | 3/2013 | Singh et al. | |
| 8,394,416 B2 | 3/2013 | Bianchi et al. | |
| 8,846,784 B2 | 9/2014 | Gäberlein et al. | |
| 9,181,364 B2 | 11/2015 | Kopping et al. | |
| 9,205,107 B2 | 12/2015 | Klaerner et al. | |
| 9,579,343 B2 | 2/2017 | Tyler et al. | |
| 9,925,214 B2 | 3/2018 | Klaerner et al. | |
| 9,931,358 B2 | 4/2018 | Tyler et al. | |
| 9,993,500 B2 | 6/2018 | Klaerner et al. | |
| 10,272,103 B2 | 4/2019 | Kopping et al. | |
| 2001/0027225 A1 | 10/2001 | Downie | |

(Continued)

FOREIGN PATENT DOCUMENTS

| | | |
|---|---|---|
| CN | 102942646 A | 2/2013 |
| CN | 103111247 A | 5/2013 |
| CN | 103724518 A | 4/2014 |
| CN | 102942646 B | 6/2016 |
| EP | 0143328 A2 | 6/1985 |
| EP | 0322736 A2 | 7/1989 |
| EP | 0143328 B1 | 6/1990 |
| EP | 0322736 B1 | 4/1993 |
| EP | 0964894 * | 12/1999 |

(Continued)

OTHER PUBLICATIONS

Australian Office Action, dated Nov. 22, 2019, for Australian Application No. 2017388956.

(Continued)

*Primary Examiner* — Danah Al-Awadi

(74) *Attorney, Agent, or Firm* — Birch, Stewart, Kolasch & Birch, LLP

(57) ABSTRACT

The object of the present invention is to provide a therapeutic agent for hyperphosphatemia capable sufficiently decreasing a serum phosphorus concentration with a small dose. The present invention provides a therapeutic agent for hyperphosphatemia, which comprises, as an active ingredient, a particle containing certain crosslinked polymer (preferably crosslinked polyallylamine).

11 Claims, 9 Drawing Sheets

(56) References Cited

U.S. PATENT DOCUMENTS

| | | |
|---|---|---|
| 2001/0041756 A1 | 11/2001 | Klix et al. |
| 2002/0122786 A1* | 9/2002 | Matsuda ............... A61K 9/2054 424/78.35 |
| 2002/0128429 A1 | 9/2002 | Rea |
| 2002/0159968 A1 | 10/2002 | Petersen et al. |
| 2002/0168333 A1 | 11/2002 | Burke |
| 2002/0182168 A1 | 12/2002 | Holmes-Farley |
| 2002/0187120 A1 | 12/2002 | Holmes-Farley et al. |
| 2002/0187121 A1 | 12/2002 | Burke |
| 2003/0039627 A1 | 2/2003 | Holmes-Farley et al. |
| 2003/0049226 A1 | 3/2003 | Burke et al. |
| 2004/0006201 A1 | 1/2004 | Stanek et al. |
| 2004/0059065 A1* | 3/2004 | Goto .................... A61K 31/785 525/326.1 |
| 2004/0166156 A1 | 8/2004 | Tyler et al. |
| 2004/0194334 A1 | 10/2004 | Rea |
| 2005/0147580 A1 | 7/2005 | Connor et al. |
| 2006/0034914 A1 | 2/2006 | Tyler et al. |
| 2006/0110488 A1 | 5/2006 | Saikin |
| 2006/0223982 A1 | 10/2006 | Rea |
| 2006/0258812 A1 | 11/2006 | Gopalkrishna et al. |
| 2007/0190135 A1 | 8/2007 | Matsuda et al. |
| 2007/0286841 A1 | 12/2007 | Burke et al. |
| 2008/0085872 A1 | 4/2008 | Burke et al. |
| 2008/0112918 A1 | 5/2008 | Holmes-Farley et al. |
| 2008/0132677 A1 | 6/2008 | Rea |
| 2008/0166317 A1* | 7/2008 | Keller .................... A01N 55/00 424/78.17 |
| 2009/0280178 A1 | 11/2009 | Hedge et al. |
| 2009/0291135 A1 | 11/2009 | Tyler et al. |
| 2010/0068167 A1 | 3/2010 | Petersen et al. |
| 2010/0083523 A1 | 4/2010 | Rea |
| 2010/0092421 A1 | 4/2010 | Hegde et al. |
| 2010/0183732 A1 | 7/2010 | Bianchi et al. |
| 2010/0189679 A1* | 7/2010 | Inoue .................... A61K 31/785 424/78.17 |
| 2010/0234490 A1 | 9/2010 | Gäberlein et al. |
| 2010/0305302 A1 | 12/2010 | Rea |
| 2010/0330175 A1 | 12/2010 | Jobdevairakkam |
| 2011/0028660 A1 | 2/2011 | Singh et al. |
| 2011/0064820 A1 | 3/2011 | Omray et al. |
| 2011/0201760 A1 | 8/2011 | Rea |
| 2012/0220731 A1 | 8/2012 | Rea |
| 2012/0322894 A1 | 12/2012 | Tyler et al. |
| 2013/0022570 A1 | 1/2013 | Kopping et al. |
| 2013/0123433 A1 | 5/2013 | Liu et al. |
| 2013/0189215 A1 | 7/2013 | Lees et al. |
| 2014/0091034 A1 | 4/2014 | Ichinose et al. |
| 2015/0056278 A1 | 2/2015 | Tyler et al. |
| 2015/0056451 A1 | 2/2015 | Klaerner et al. |
| 2015/0329842 A1 | 11/2015 | Cascao-Pereira et al. |
| 2016/0051576 A1 | 2/2016 | Kopping et al. |
| 2016/0074430 A1 | 3/2016 | Klaerner et al. |
| 2017/0183425 A1 | 6/2017 | Ishii et al. |
| 2017/0202872 A1 | 7/2017 | Tyler et al. |
| 2018/0015119 A1 | 1/2018 | Kumar et al. |
| 2018/0015121 A1 | 1/2018 | Klaerner et al. |
| 2018/0021370 A1 | 1/2018 | Klaerner et al. |
| 2018/0280428 A1 | 10/2018 | Klaerner et al. |
| 2019/0315932 A1 | 10/2019 | Tokuoka et al. |

FOREIGN PATENT DOCUMENTS

| | | |
|---|---|---|
| EP | 0997148 A1 | 5/2000 |
| EP | 0716606 B1 | 8/2001 |
| EP | 1133989 A2 | 9/2001 |
| EP | 1153940 A1 | 11/2001 |
| EP | 1304104 A2 | 4/2003 |
| EP | 0997148 B1 | 7/2003 |
| EP | 1123330 B1 | 3/2004 |
| EP | 1319029 B1 | 1/2005 |
| EP | 1133989 B1 | 5/2006 |
| EP | 1379258 B1 | 6/2006 |
| EP | 1676581 A2 | 7/2006 |
| EP | 1304104 B1 | 6/2007 |
| EP | 1175451 B1 | 7/2007 |
| EP | 1416942 B1 | 12/2007 |
| EP | 1881013 A1 | 1/2008 |
| EP | 1442073 B1 | 3/2008 |
| EP | 1392331 B1 | 4/2008 |
| EP | 1918318 A1 | 5/2008 |
| EP | 1923064 A2 | 5/2008 |
| EP | 2016947 A1 | 1/2009 |
| EP | 1214359 B1 | 3/2009 |
| EP | 1918318 B1 | 2/2010 |
| EP | 2172204 A1 | 4/2010 |
| EP | 4547620 B2 | 9/2010 |
| EP | 2175866 B1 | 12/2010 |
| EP | 2441779 A1 | 4/2012 |
| EP | 2481414 A1 | 8/2012 |
| EP | 2719730 A1 | 4/2014 |
| EP | 2539380 B1 | 8/2015 |
| EP | 2998329 A2 | 3/2016 |
| EP | 2538947 B1 | 8/2016 |
| EP | 3130343 A1 | 2/2017 |
| EP | 1923064 B1 | 6/2017 |
| EP | 3003327 B1 | 8/2017 |
| EP | 3287133 A1 | 2/2018 |
| EP | 3130343 B1 | 5/2018 |
| EP | 3287133 B1 | 4/2019 |
| EP | 3 564 292 A1 | 11/2019 |
| EP | 3 698 798 A1 | 8/2020 |
| JP | 61-51006 A | 3/1986 |
| JP | 63-45721 B2 | 9/1988 |
| JP | 4-8710 A | 1/1992 |
| JP | 10-330269 A | 12/1998 |
| JP | 10-330427 A | 12/1998 |
| JP | 2001-516787 A | 10/2001 |
| JP | 2004-59747 A | 2/2004 |
| JP | 2006-169292 A | 6/2006 |
| JP | 2007-530737 A | 11/2007 |
| JP | 2008-533272 A | 8/2008 |
| JP | 2009-132700 A | 6/2009 |
| JP | 2011-94128 A | 5/2011 |
| JP | 2012-121989 A | 6/2012 |
| JP | 2012-153747 A | 8/2012 |
| JP | 2012-531415 A | 12/2012 |
| JP | 2013-209617 A | 10/2013 |
| JP | 6792640 B2 | 11/2020 |
| WO | WO 95/05184 A2 | 2/1995 |
| WO | WO 98/37149 A1 | 8/1998 |
| WO | WO 98/44933 A1 | 10/1998 |
| WO | WO 99/14275 A1 | 3/1999 |
| WO | WO 99/47587 A1 | 9/1999 |
| WO | WO 00/22008 A1 | 4/2000 |
| WO | WO 00/22017 A1 | 4/2000 |
| WO | WO 00/59996 A1 | 10/2000 |
| WO | WO 00/63259 A1 | 10/2000 |
| WO | WO 01/18072 A1 | 3/2001 |
| WO | WO 01/18073 A1 | 3/2001 |
| WO | WO 02/22695 A1 | 3/2002 |
| WO | WO 02/066543 A1 | 8/2002 |
| WO | WO 02/085377 A1 | 10/2002 |
| WO | WO 02/085378 A1 | 10/2002 |
| WO | WO 02/085379 A1 | 10/2002 |
| WO | WO 02/085380 A1 | 10/2002 |
| WO | WO 02/085381 A1 | 10/2002 |
| WO | WO 02/085382 A1 | 10/2002 |
| WO | WO 02/085383 A1 | 10/2002 |
| WO | WO 03/031501 A1 | 4/2003 |
| WO | WO 2005/041900 A2 | 5/2005 |
| WO | WO 2005/041902 A2 | 5/2005 |
| WO | WO 2006/097942 A1 | 9/2006 |
| WO | WO 2007/017286 A1 | 2/2007 |
| WO | WO 2007/056405 A2 | 5/2007 |
| WO | WO 2008/062437 A2 | 5/2008 |
| WO | WO 2009/008480 A1 | 1/2009 |
| WO | WO 2009/010531 A1 | 1/2009 |
| WO | WO 2009/078956 A1 | 6/2009 |
| WO | WO 2009/128085 A1 | 10/2009 |
| WO | WO 2011/106542 A2 | 9/2011 |
| WO | WO 2011/106545 A1 | 9/2011 |
| WO | WO 2012/042542 A1 | 4/2012 |

(56) References Cited

FOREIGN PATENT DOCUMENTS

| WO | WO 2012/173031 A1 | 12/2012 |
|---|---|---|
| WO | WO 2013/087238 A1 | 6/2013 |
| WO | WO 2014/197725 A1 | 12/2014 |
| WO | WO 2015/156251 A1 | 10/2015 |
| WO | WO 2016/094685 A1 | 6/2016 |
| WO | WO 2016/135065 A1 | 9/2016 |
| WO | WO 2018/124264 A1 | 7/2018 |

OTHER PUBLICATIONS

Fissell et al., "Phosphate Binder Pill Burden, Patient-Reported Non-Adherence, and Mineral Bone Disorder Markers: Findings from the DOPPS", Hemodial Int. Author Manuscript, vol. 20, No. 1, Jan. 2016, pp. 38-49 (20 pages).
Inoue et al., "Highly Selective and Low-swelling Phosphate-binding Polymer for Hyperphosphatemia Therapy", Chem. Letter, vol. 41, 2012, pp. 932-933 (2 pages).
International Preliminary Report on Patentabillty and Written Opinion or the International Searchlng Authority(Forms PCT/IB/373 and PCT/ISA/237), dated Jul. 2, 2019, for International Application No. PCT/JP2017/047178, with an English Translation of the Written Opinion.
International Search Report (Form PCT/ISA/210), dated Apr. 3, 2018, for International Application No. PCT/JP2017/047178, with an English translation.
International Search Report (Form PCT/ISA/210 & PCT/ISA/220), dated Nov. 27, 2018, for International Application No. PCT/JP2018/038465, with an English translation.
Written Opinion of the International Searching Authority(Form PCT/ISA/237), dated Nov. 27, 2018, for International Application No. PCT/JP2018/038465, with an English translation.
Zhang et al, "Facile preparation and evaluation of allylamine hydrochloride-based porous hydrogel without calcium and aluminum; an alternative candidate of phosphate binder", Polym. Bull, vol. 73, 2016 published online Apr. 11, 2016), pp. 3371-3384 (16 pages).
United States Office Action for U.S. Appl. No. 16/457,338, dated Dec. 23, 2019.
Extended European Search Report, dated Dec. 6, 2019, for European Application No. 17888776.6.
Indian Bibliographical Data and Specification, dated Nov. 1, 2013, for Indian Application No. 1928/MUM/2011.
U.S. Office Action, dated Apr. 3, 2020, for U.S. Appl. No. 16/457,338.
Extended European Search Report for corresponding European Application No. 18869094.5, dated Oct. 26, 2020.
Indian Office Action dated Aug. 4, 2020 issued in the Indian patent application No. 202047016500.
Indian Office Action dated Jul. 15, 2020 issued in the Indian patent application No. 201947025894.
Japanese Office Action dated Jul. 14, 2020 issued in the Japanese patent application No. 20718-559628 with its English Machine Translation.
U.S. Office Action for U.S. Appl. No. 16/455,091, dated Jan. 8, 2021.
Extended European Search Report for European Application No. 18868309.8 dated Nov. 23, 2020.
United States Office Action for U.S. Appl. No. 16/457,338, dated Oct. 16, 2020.
Japanese Office Action, dated Apr. 20, 2020, for Japanese Application No. 2019-549288, with an English machine translation.
Japanese Office Action, dated Apr. 20, 2020, for Japanese Application No. 2019-549289, with an English machine translation.
U.S. Appl. No. 16/457,338, filed Jun. 28, 2019.
U.S. Appl. No. 16/455,091, filed Jun. 27, 2019.
Australian Office Action for Australian Application No. 2018352766, dated Mar. 2, 2021.
Canadian Office Action for Canadian Application No. 3,079,171, dated May 21, 2021.
Chinese Office Action and Search Report for Chinese Application No. 201780080982.1, dated May 24, 2021, with English translation of the Office Action.
Indian Hearing Notice, dated Jul. 23, 2021, for Indian Application No. 202047016500, with an English translation.
Decision of Dismissal of Admendment dated Sep. 7, 2021 issued in the related Japanese patent application No. 2019-549289 with its English Machine Translation.
Decision of Refusal dated Sep. 7, 2021 issued in the related Japanese patent application No. 2019-549289 with its English Machine Translation.

\* cited by examiner

[Figure 1]
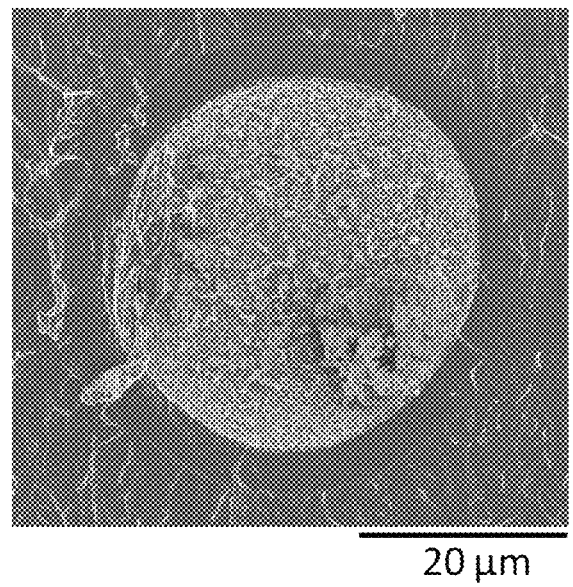
[Figure 2]
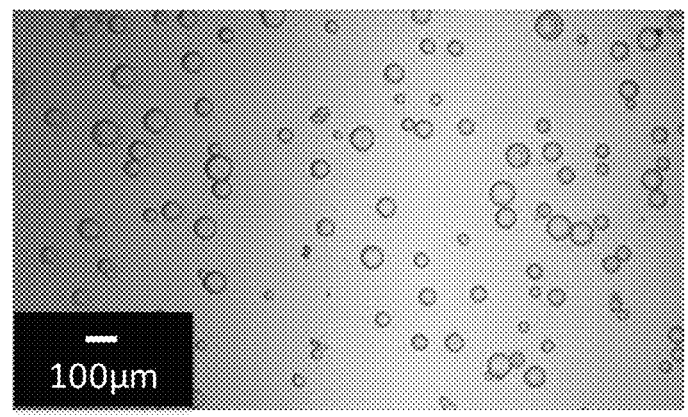

[Figure 3]
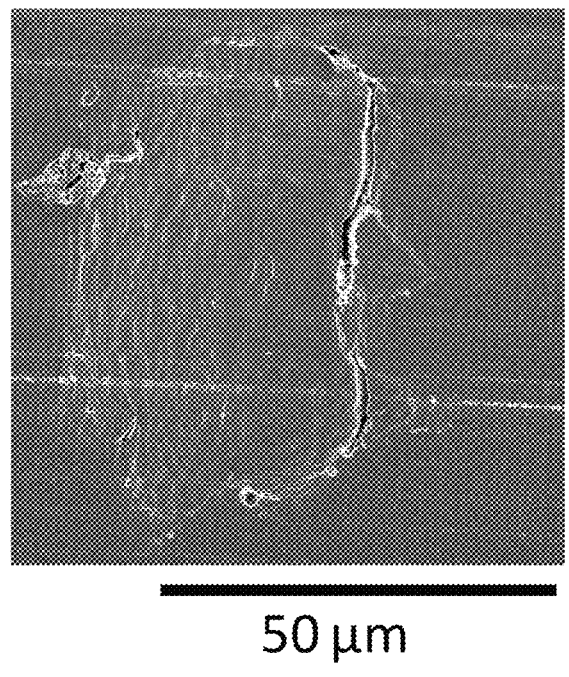
50 μm
[Figure 4]
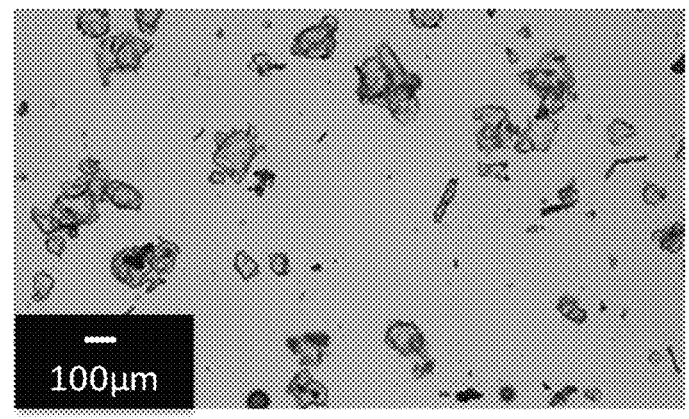

[Figure 5]
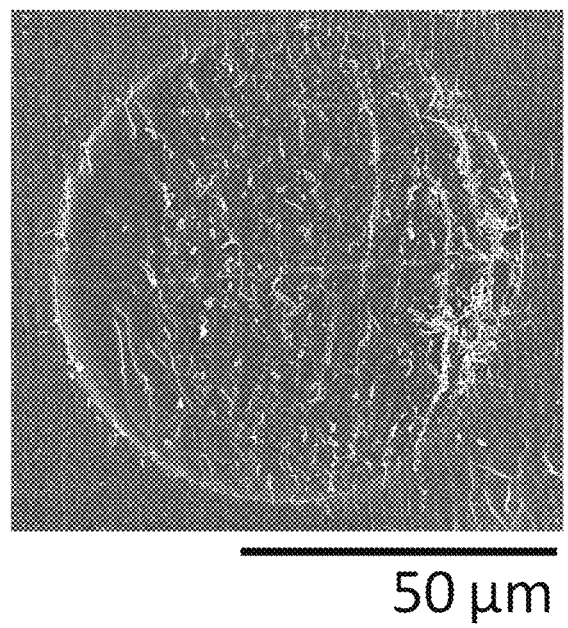
50 μm
[Figure 6]
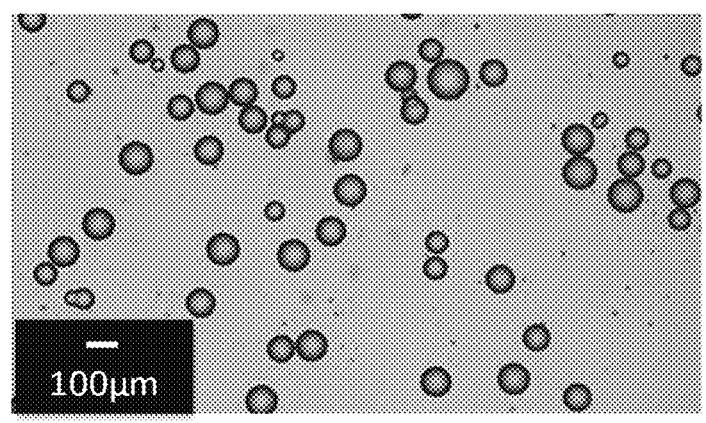

[Figure 7]
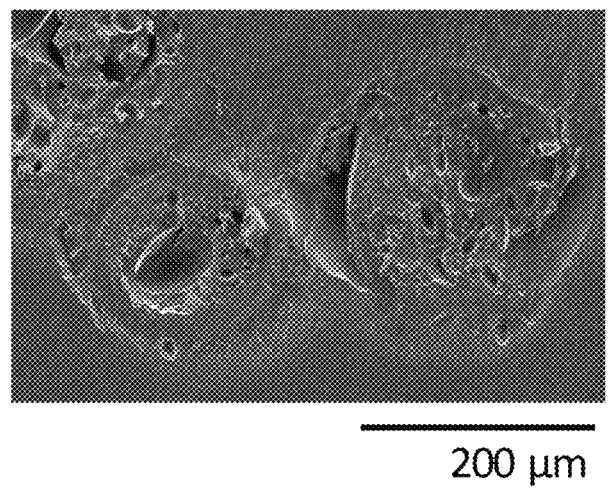
200 μm
[Figure 8]
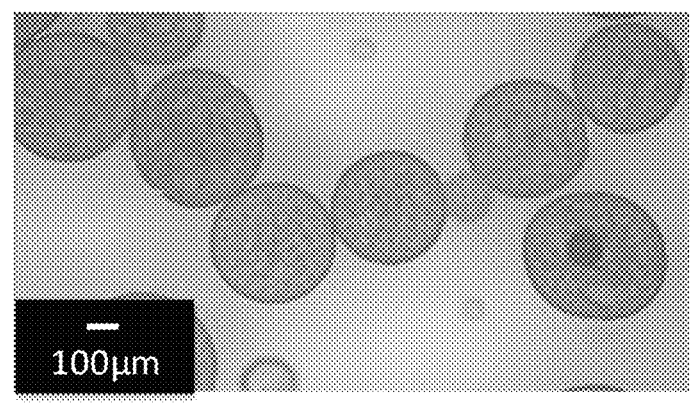
100μm

[Figure 9]
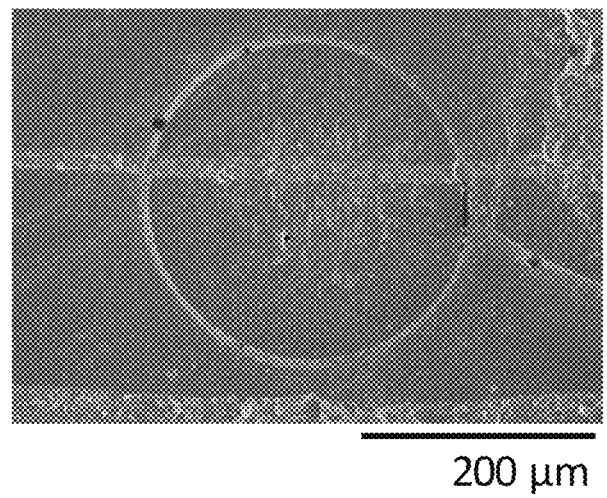
200 μm
[Figure 10]
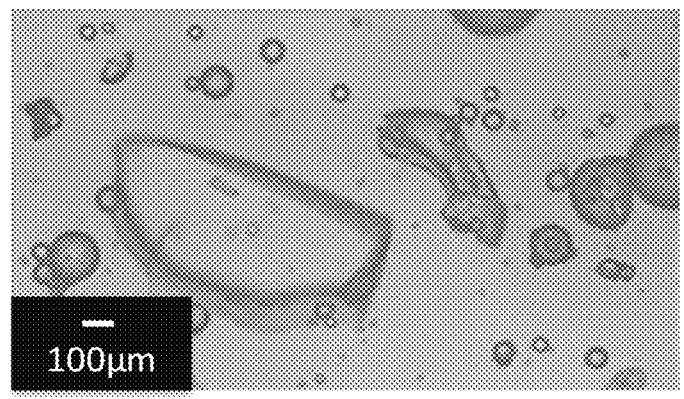

[Figure 11]
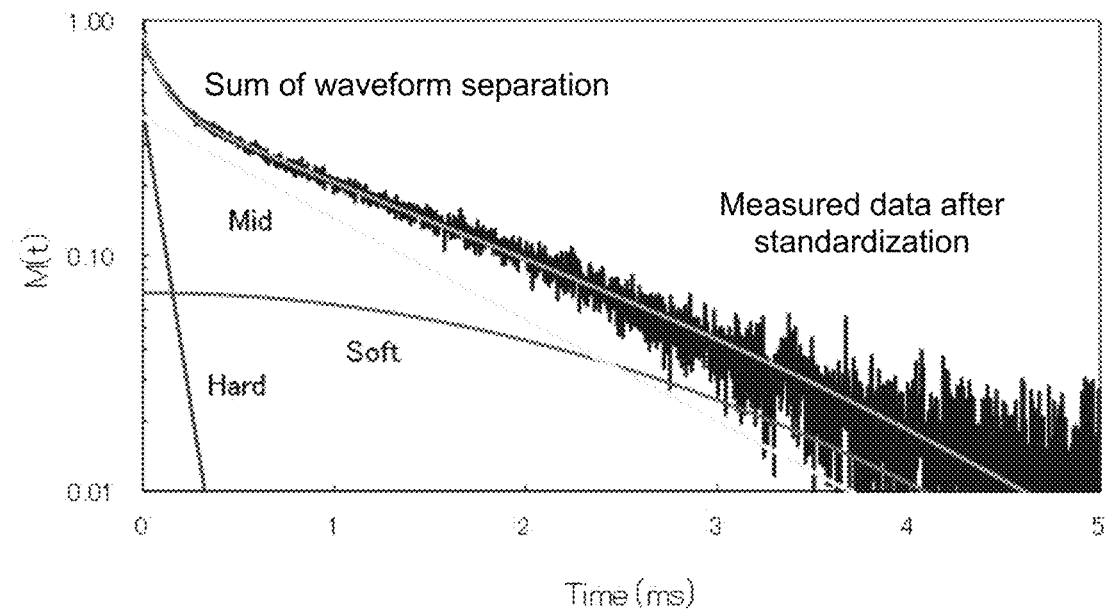
[Figure 12]
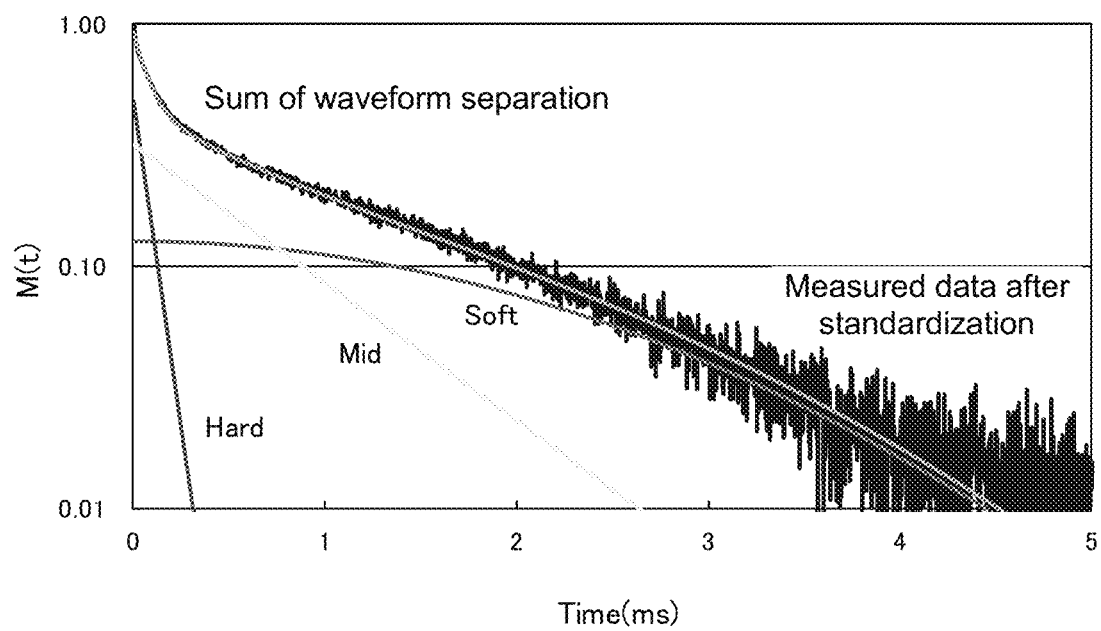

[Figure 13]
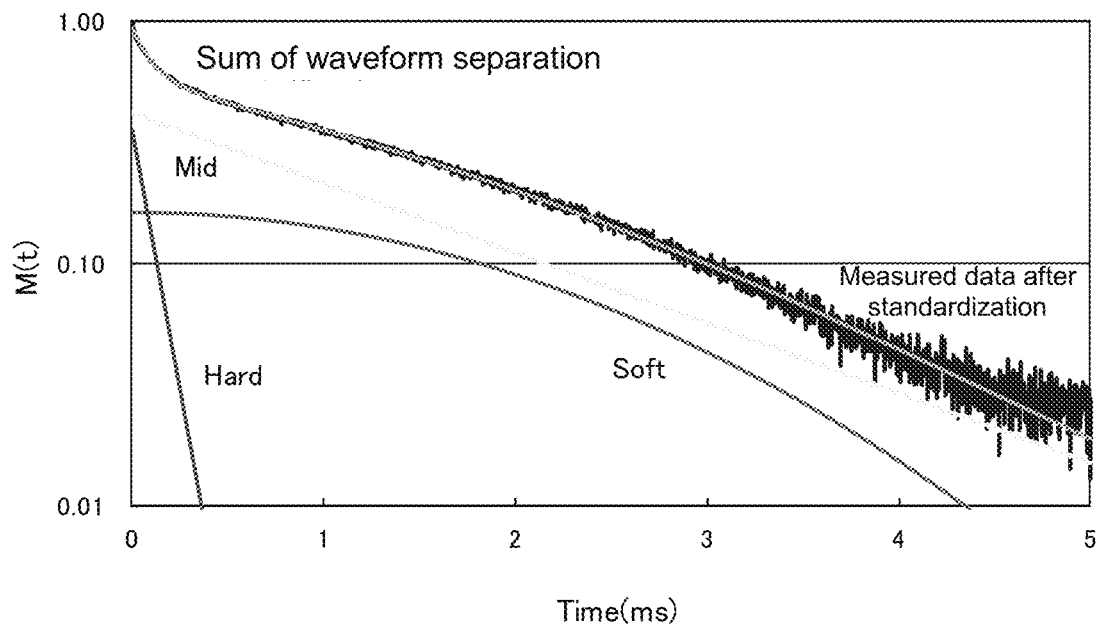
[Figure 14]
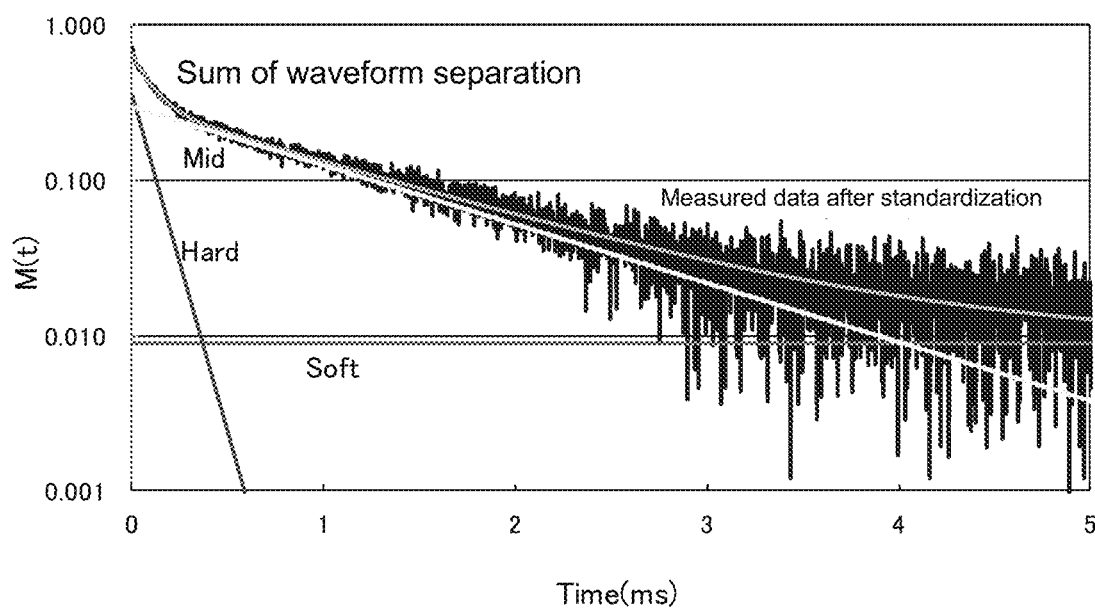

[Figure 15]
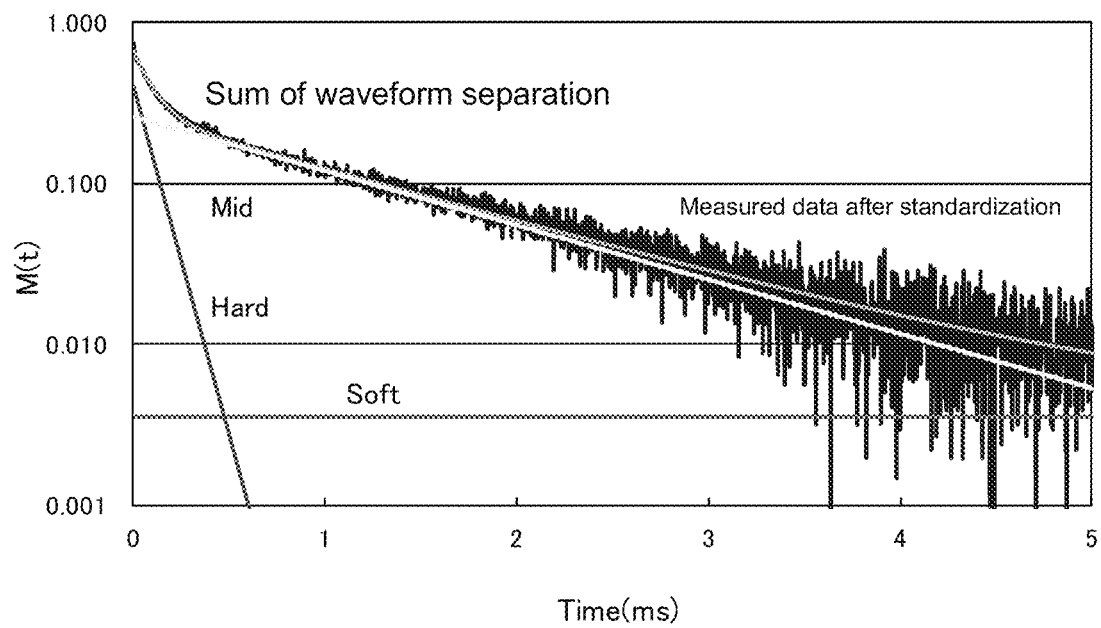
[Figure 16]
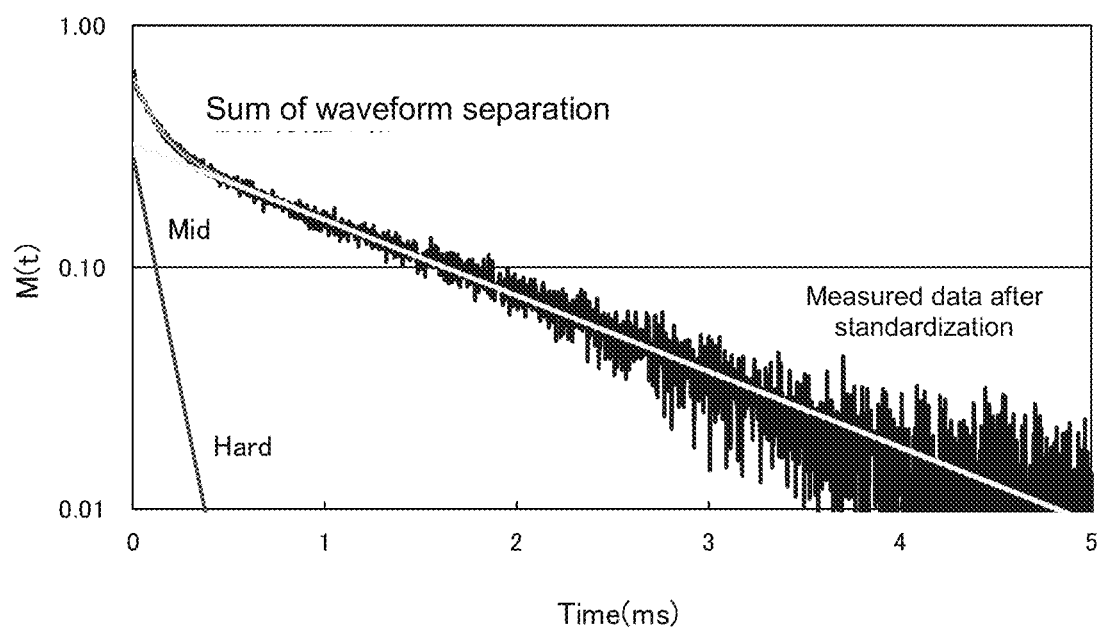

[Figure 17]
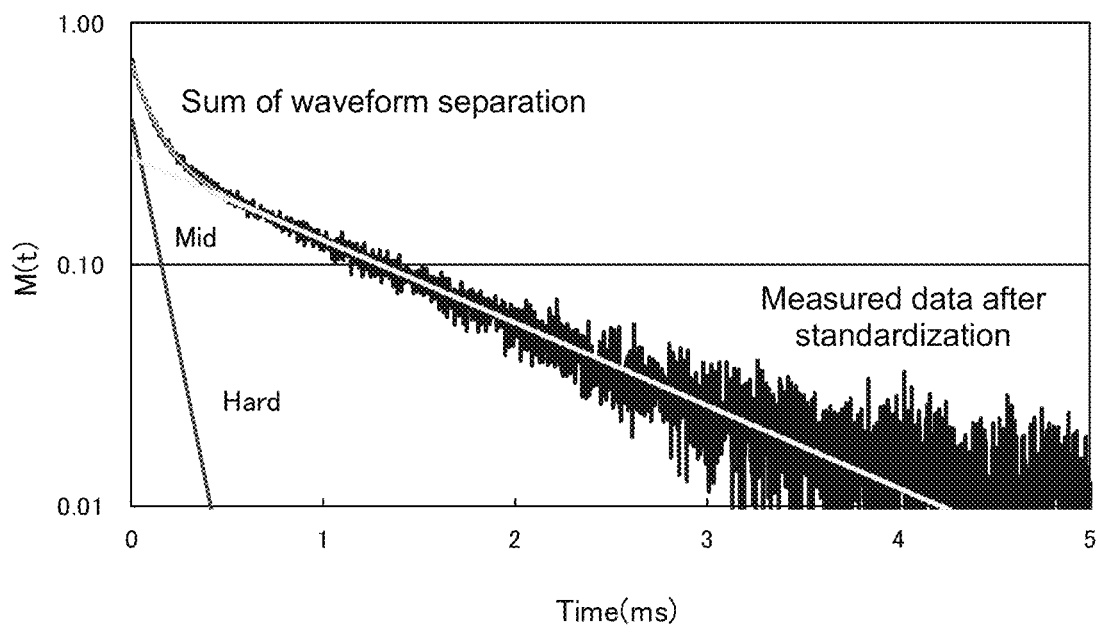
[Figure 18]
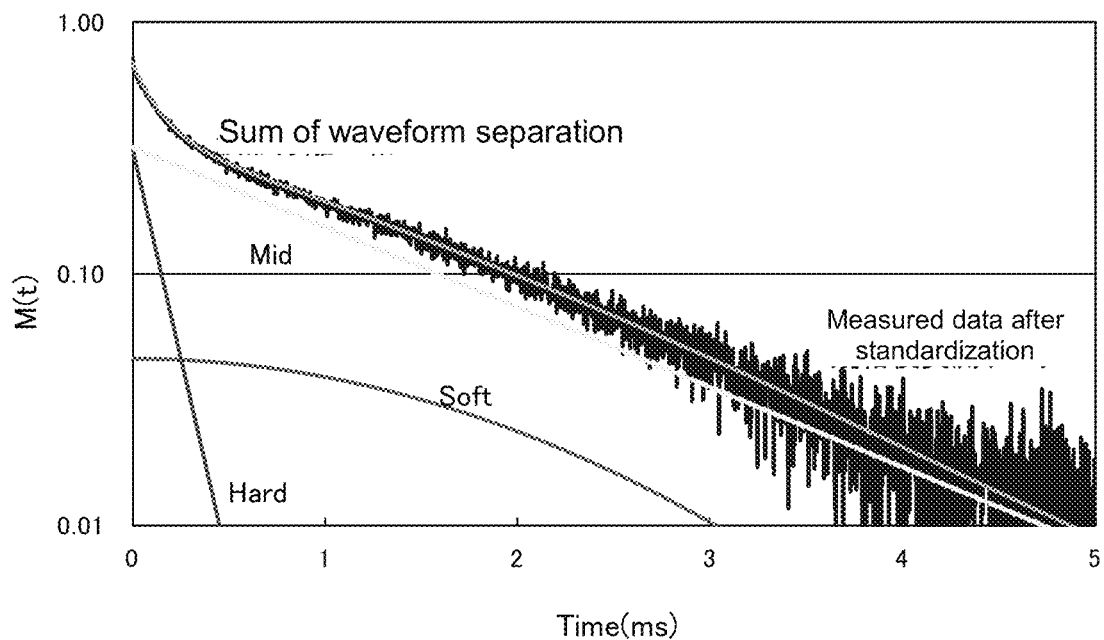

THERAPEUTIC AGENT FOR HYPERPHOSPHATEMIA

CROSS-REFERENCE TO RELATED APPLICATIONS

This application is a Continuation of PCT International Application No. PCT/JP2018/38465 filed on Oct. 16, 2018, which claims priority under 35 U.S.C § 119(a) to Japanese Patent Applications No. 2017-200016 filed on Oct. 16, 2017, No. 2017-252895 filed on Dec. 28, 2017, and No. 2018-121071 filed on Jun. 26, 2018. Each of the above application(s) is hereby expressly incorporated by reference, in its entirety, into the present application.

TECHNICAL FIELD

The present invention relates to a therapeutic agent for hyperphosphatemia comprising crosslinked polymer-containing particles as an active ingredient.

BACKGROUND ART

Chronic kidney disease (CKD) patients and dialysis patients are often prescribed with many medications and are likely to deteriorate the medication adherence. An adherence decrease on polymer-based phosphorus adsorption agents, whose doses are the highest among agents to be taken, is associated with a high value of serum phosphorus, a high value of parathyroid hormone (PTH) and the deterioration of quality of life (QOL). An adherence decrease is also attributable to high doses (see, for example, Non Patent Literature 1).

As a phosphorus adsorption agent for the treatment of hyperphosphatemia in CKD patients and dialysis patients, used are metal-based phosphorus adsorption agents such as calcium carbonate and lanthanum carbonate; and polymer-based phosphorus adsorption agents such as Sevelamer hydrochloride and Bixalomer. These therapeutic agents all exhibit a serum phosphorus concentration lowering effect by adsorbing phosphorus in taken foods in the gastrointestinal tract.

Sevelamer hydrochloride is a crosslinked polymer obtained by reaction of a polyallylamine (prop-2-en-amine polymer) and epichlorohydrin (1-chloro-2,3-epoxypropane) (see, for example, Patent Literatures 1 to 7). Patent Literature 1 discloses in claim 3 a crosslinking agent such as epichlorohydrin, and Patent Literatures 1 to 3 disclose that epichlorohydrin is used as a crosslinking agent in their Examples. Patent Literatures 2 to 3 disclose in their Examples that Sevelamer hydrochloride is produced by crushing or grinding at a final stage. Patent literatures 4 to 5 also disclose in their Examples that epichlorohydrin is used as a crosslinking agent, and Sevelamer hydrochloride is produced by crushing the epichlorohydrin.

There is a case that Sevelamer hydrochloride is prepared, for example, as a form of an emulsified particle in a medium. In Patent Literatures 4 to 5, a crosslinking agent is added to an emulsified polyallylamine hydrochloride to produce a crosslinked polyallylamine polymer. As the crosslinking agent, epichlorohydrin is used.

Sevelamer hydrochloride is a crosslinked polyallylamine particle, and a crosslinked polyallylamine particle itself has been known since early times (see, for example, Patent Literature 8). Patent Literature 8 describes a method for producing a small-globular crosslinked monoallylamine polymer, which includes emulsifying an aqueous solution of a monoallylamine polymer in a liquid medium, and cross-linking a part of amino groups present in the polymer with a predetermined compound while the emulsified state is maintained. In Example 1 of Patent Literature 8, dibromohexane is used as the crosslinking agent. Further, Patent Literature 9 discloses that a macromolecular gelated allylamine-based polymer is demanded in the pharmaceutical field for cholesterol-lowering agents, phosphate removers and the like, and it describes a method for producing a macromolecular gelated allylamine-based polymer, wherein 1,6-diamino-n-hexane is used as a crosslinking agent.

It is known that a crosslinked polyallylamine particle is used as a bile acid binding agent (see, for example, Patent Literature 10). Patent Literature 10 discloses a crosslinked amine polymer, which is crosslinked with a C5 to C12 alkylene (see paragraphs 0007 and 0155). It discloses in Example 10 that dibromooctane is used as a crosslinking agent and grinding is carried out at a final stage for production. As to the polymer described in Patent Literature 10, it is described that the amount of the polymer which was bound to phosphate is small (see paragraph 0049).

Also, Bixalomer is a crosslinked polymer obtained by reaction of N,N,N',N'-tetrakis (3-aminopropyl) 1,4-butanediamine and 2-(chloromethyl)oxirane in a ratio of 1:2.1 to 2.4 (see, for example, Patent Literatures 11 to 12).

PRIOR ART LITERATURES

Non Patent Literatures

Non Patent Literature 1: Fissell R B, et al., Hemodial Int., Vol. 20 (1), pages 38 to 49, 2016

Patent Literatures

Patent Literature 1: International Publication No. WO95/05184 pamphlet
Patent Literature 2: International Publication No. WO2001018072 pamphlet
Patent Literature 3: International Publication No. WO2002085378 pamphlet
Patent Literature 4: International Publication No. WO0022008 pamphlet
Patent Literature 5: JP Patent Publication (Kokai) No. 10-330269 A (1998)
Patent Literature 6: International Publication No. WO2006097942 pamphlet
Patent Literature 7: International Publication No. WO2008062437 pamphlet
Patent Literature 8: JP Patent Publication (Kokoku) No. 63-45721 B (1988)
Patent Literature 9: JP Patent Publication (Kokai) No. 10-330427 (1998)
Patent Literature 10: International Publication No. WO2011106542 pamphlet
Patent Literature 11: International Publication No. WO2005041902 pamphlet
Patent Literature 12: JP Patent Publication (Kokai) No. 2009-132700

SUMMARY OF INVENTION

Objects to be Solved by the Invention

As current therapeutic agents for hyperphosphatemia, metal-based phosphorus adsorption agents or polymer-based phosphorus adsorption agents are clinically applied. However, there is a concern that metal-based phosphorus adsorption agents may cause accumulation of metals in the body, and polymer-based phosphorus adsorption agents disadvantageously need to be taken in a large amount.

The package insert of Sevelamer hydrochloride indicates that a dosage thereof is 3 to 9 g/day, and the number of tablets to be taken is 12 to 36 tablets per day. Sevelamer hydrochloride is an agent that gives a large burden on dialysis patients in terms of the amount of agent to be taken in the defined dose.

The package insert of Bixalomer indicates that a dosage thereof is 1.5 to 7.5 g/day and the number of capsules to be taken is 6 to 30 capsules per day. Like Sevelamer hydrochloride, Bixalomer is an agent that causes a large burden on dialysis patients in terms of the amount of agent to be taken.

From these current situations, there is a need for a polymer-based phosphorus adsorption agent for the treatment of hyperphosphatemia in medical front, wherein even a small dose thereof can control a serum phosphorus concentration.

The object to be solved by the present invention is to provide a therapeutic agent for hyperphosphatemia capable of sufficiently decreasing a serum phosphorus concentration with a small dose.

Means for Solving the Object

The present inventors have made intensive studies to solve the above object. As a result, they have found that use of a therapeutic agent for hyperphosphatemia comprising, as an active ingredient, particles which contain a crosslinked polymer which is obtained by using certain cross-linking agent, can sufficiently decrease a serum phosphorus concentration even when a dose thereof is small. The present invention has been completed based on these findings.

That is, the present invention provides the following inventions.

<1> A therapeutic agent for hyperphosphatemia which comprises, as an active ingredient, a particle comprising a crosslinked polymer having at least a repeating unit A represented by the following formula (1-1) or (1-2) and a repeating unit B represented by the following formula (2-1) or (2-2),

[Formula 1]

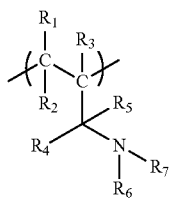
(1-1)

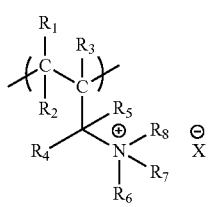
(1-2)

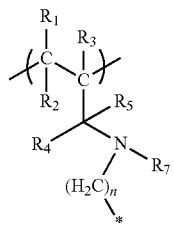
(2-1)

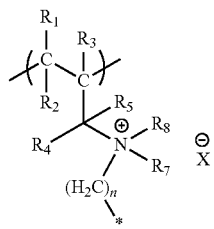
(2-2)

wherein:
$R_1$, $R_2$, $R_3$, $R_4$ and $R_5$ each independently represent a hydrogen atom, a halogen atom, or an alkyl group having 1 to 20 carbon atoms;
$R_6$, $R_7$ and $R_8$ each independently represent a hydrogen atom, an alkyl group having 1 to 20 carbon atoms, an aminoalkyl group having 1 to 20 carbon atoms or a salt thereof, an alkylaminoalkyl group having 2 to 20 carbon atoms or a salt thereof, a dialkylaminoalkyl group having 3 to 20 carbon atoms or a salt thereof, a trialkylammoniumalkyl group having 4 to 20 carbon atoms, an alkylcarbonyl group having 1 to 20 carbon atoms, a carboxyalkyl group having 1 to 20 carbon atoms, or a hydroxyalkyl group having 1 to 20 carbon atoms;
$X^-$ is a negatively charged counter ion,
n represents an integer of 5 to 7,
symbol * denotes a bond with a nitrogen atom on the side chain of the repeating unit A, and in this case, at least one of $R_6$, $R_7$ and $R_8$ is a bond.
<2> The therapeutic agent for hyperphosphatemia according to <1>, wherein n is 6.
<3> The therapeutic agent for hyperphosphatemia according to <1> or <2>,
wherein:
$R_1$, $R_2$, $R_3$, $R_4$ and $R_5$ each independently represent a hydrogen atom or an alkyl group having 1 to 20 carbon atoms; and
$R_6$, $R_7$ and $R_8$ each independently represent a hydrogen atom or an alkyl group having 1 to 20 carbon atoms.
<4> The therapeutic agent for hyperphosphatemia according to any one of <1> to <3>,
wherein:
$R_1$, $R_2$, $R_3$, $R_4$ and $R_5$ represent a hydrogen atom; and
$R_6$, $R_7$ and $R_8$ represent a hydrogen atom.
<5> The therapeutic agent for hyperphosphatemia according to any one of <1> to <4>, wherein the particle has an average particle diameter of 20 to 150 μm,
wherein the average particle diameter is calculated as a volume average particle diameter by converting an area of 1000 or more imaged particles dispersed in water in an optical microscope photograph to diameters and using the diameters.
<6> The therapeutic agent for hyperphosphatemia according to any one of <1> to <5>, wherein the particle has a swelling rate of 8 to 20 mL/g, wherein the swelling rate is calculated by dividing, by a mass of the particle before swelling, a volume of the swollen particle which is obtainable by repeating shaking and 1-hour or longer still standing 20 or more times in an aqueous solution containing 2.2% by mass of sodium 2-morpholinoethanesulfonate and 0.5% by mass of sodium chloride and having a pH of 6.3 at 20° C.

<7> The therapeutic agent for hyperphosphatemia according to any one of <1> to <6>, wherein the particle is a globule.

<8> The therapeutic agent for hyperphosphatemia according to any one of <1> to <7>, wherein the content of the repeating unit A in all the crosslinked polymers is 90 to 99% by mole, and the content of the repeating unit B in all the crosslinked polymers is 1 to 10% by mole.

<9> The therapeutic agent for hyperphosphatemia according to any one of <1> to <8>, wherein when a free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the particle has a proportion of a semi-restrained part of 25 to 70%.

<10> The therapeutic agent for hyperphosphatemia according to any one of <1> to <9>, wherein when a free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the particle has a proportion of the restrained part of 30 to 70%.

<11> The therapeutic agent for hyperphosphatemia according to any one of <1> to <10> wherein a phosphate adsorption capacity is 6.0 to 10.0 mmol/g, wherein the phosphate adsorption capacity is calculated by: when 30 mg of particles is mixed and stirred at 37° C. for 1 hour in 20 mL of aqueous solution containing 2.2% by mass of sodium morpholinoethanesulfonate, 0.47% by mass of sodium chloride and 0.24% by mass of phosphate and having a pH of 6.4, quantifying phosphate concentrations in a supernatant before and after mixing by ICP emission spectrochemical analysis; dividing a decrease thereof by a mass of the particles; and correcting by use of a loss on drying.

<12> The therapeutic agent for hyperphosphatemia according to any one of <1> to <11> wherein an amine value is 11.0 to 17.5 mmol/g, wherein the amine value is calculated by: treating particles dispersed in ultrapure water with 5 N hydrochloric acid; quantifying an amino group by conducting neutralization titration with 0.1 N sodium hydroxide aqueous solution; dividing by a mass of the particles; and correcting by use of a loss on drying.

The present invention further provides the following.

<A> A method for treating hyperphosphatemia, which comprises administering a particle containing the above crosslinked polymer to a subject (mammals including humans, preferably humans).

<B> A particle containing the above crosslinked polymer for use in the treatment of hyperphosphatemia.

<C> Use of the particles containing the above crosslinked polymer for the production of a therapeutic agent for hyperphosphatemia.

Advantageous Effects of Invention

The present invention provides a polymer-based therapeutic agent for hyperphosphatemia, which can sufficiently decrease a serum phosphorus concentration with a small dose. In addition, the present invention contributes to the improvement in the prognosis and QOL (quality of life) of CKD patients and dialysis patients.

BRIEF DESCRIPTION OF DRAWINGS

FIG. 1 shows a scanning electron microscope image in Example 1-1.
FIG. 2 shows an optical microscope photograph in Example 1-1.
FIG. 3 shows a scanning electron microscope image of Sevelamer hydrochloride in Comparative Examples 1 and 2.
FIG. 4 shows an optical microscope photograph of Sevelamer hydrochloride in Comparative Examples 1 and 2.
FIG. 5 shows a scanning electron microscope image of Bixalomer in Comparative Examples 3 and 4.
FIG. 6 shows an optical microscope photograph of Bixalomer in Comparative Examples 3 and 4.
FIG. 7 shows a scanning electron microscope image in Comparative Example 5.
FIG. 8 shows an optical microscope photograph in Comparative Example 5.
FIG. 9 shows a scanning electron microscope image in Comparative Example 6.
FIG. 10 shows an optical microscope photograph in Comparative Example 6.
FIG. 11 shows an attenuation curve of pulse NMR in Example 1-1.
FIG. 12 shows an attenuation curve of pulse NMR in Example 2.
FIG. 13 shows an attenuation curve of pulse NMR in Example 3.
FIG. 14 shows an attenuation curve of pulse NMR in Example 11.
FIG. 15 shows an attenuation curve of pulse NMR in Example 19.
FIG. 16 shows an attenuation curve of pulse NMR in Example 20.
FIG. 17 shows an attenuation curve of pulse NMR in Example 21.
FIG. 18 shows an attenuation curve of pulse NMR in Example 22.

EMBODIMENTS FOR CARRYING OUT THE INVENTION

Hereinafter, embodiments of the present invention will be described in detail.

In the present invention, the terms have the following meanings unless otherwise specified.

In the present invention, the numerical range indicated with the term "to" means a range including numerical values written before and after the term "to" as a minimum value and a maximum value, respectively.

The halogen atom means an atom of fluorine, chlorine, bromine or iodine.

The alkyl group having 1 to 20 carbon atoms ($C_{1-20}$ alkyl group) means a linear or branched $C_{1-20}$ alkyl group such as a methyl, ethyl, propyl, isopropyl, butyl, sec-butyl, isobutyl, tert-butyl, pentyl, isopentyl, 2-methylbutyl, 2-pentyl, 3-pentyl or hexyl group. The number of carbon atoms of the alkyl group is preferably 1 to 10, more preferably 1 to 6, still more preferably 1 to 3.

The alkylamino group having 1 to 20 carbon atoms (C1-20 alkylamino group) means a linear or branched C1-20 alkylamino group such as a methylamino, ethylamino, propylamino, isopropylamino, cyclopropylamino, butylamino, sec-butylamino, tert-butylamino, cyclobutylamino, pentylamino, cyclopentylamino, hexylamino or cyclohexylamino group. The number of carbon atoms is preferably 1 to 10, more preferably 1 to 6, still more preferably 1 to 3.

The dialkylamino group having 2 to 20 carbon atoms (di(C1-20 alkyl)amino group) means a linear or branched di(C1-20 alkyl)amino group such as a dimethylamino, diethylamino, dipropylamino, diisopropylamino, dibutylamino, di(tert-butyl)amino, dipentylamino, dihexylamino, (ethyl)(methyl)amino, (methyl)(propyl)amino, (cyclopropyl)(methyl)amino, (cyclobutyl)(methyl)amino or (cyclohexyl)(methyl)amino group. The number of carbon atoms is preferably 2 to 10, more preferably 2 to 6. The alkyl groups in the dialkylamino group may be the same or different.

The aminoalkyl group having 1 to 20 carbon atoms is a group in which at least one hydrogen atom of the alkyl group having 1 to 20 carbon atoms is substituted with an amino group, preferably a group in which a hydrogen atom on the carbon atom at the terminal of the alkyl group is substituted with an amino group. The number of carbon atoms is preferably 1 to 10, more preferably 1 to 6, still more preferably 1 to 3.

The alkylaminoalkyl group having 2 to 20 carbon atoms is a group in which a hydrogen atom of an amino group in an aminoalkyl group is substituted with an alkyl, and the sum of the numbers of carbon atoms of two alkyls is within a range of 2 to 20. The number of carbon atoms is preferably 2 to 10, more preferably 2 to 6.

The dialkylaminoalkyl group having 3 to 20 carbon atoms is a group in which two hydrogen atoms of an amino group in an aminoalkyl group are each substituted with an alkyl, and the sum of the numbers of carbon atoms of three alkyls is within a range of 3 to 20. The number of carbon atoms is preferably 3 to 10, more preferably 3 to 6. The alkyls in the dialkylaminoalkyl group may be the same or different.

The salt of an aminoalkyl group having 1 to 20 carbon atoms, the salt of an alkylaminoalkyl group having 2 to 20 carbon atoms, or the salt of a dialkylaminoalkyl group having 3 to 20 carbon atoms means that a nitrogen atom in the aminoalkyl group, the alkylaminoalkyl group or the dialkylaminoalkyl group forms an ammonium salt. Examples of the ammonium salt include salts of organic acids and inorganic acids, examples of the organic acid include formic acid, acetic acid, oxalic acid, succinic acid and citric acid, and examples of the inorganic acid include hydrochloric acid, carbonic acid, sulfuric acid, nitric acid and phosphoric acid.

The trialkylammoniumalkyl group having 4 to 20 carbon atoms is a group in which at least one hydrogen atom of an alkyl group having 1 to 16 (preferably 1 to 10, more preferably 1 to 6) carbon atoms among the alkyl groups having 1 to 20 carbon atoms is substituted with a trialkylammonium group, preferably a group in which a hydrogen atom on the carbon atom at the terminal of the alkyl group is substituted. The alkyl group of the trialkylammonium group is an alkyl group having 1 to 8 (preferably 1 to 6, more preferably 1 to 3) carbon atoms. The alkyls in the trialkylammoniumalkyl group may be the same or different.

The alkylcarbonyl group having 1 to 20 carbon atoms is a group in which a carbonyl group is substituted with an alkyl group having 1 to 20 carbon atoms. The number of carbon atoms is preferably 1 to 10, more preferably 1 to 6. Specific examples of the alkylcarbonyl group include acetyl, propionyl, butyryl, isobutyryl and pivaloyl groups.

Specifically, the carboxyalkyl group having 1 to 20 carbon atoms is $-(CH_2)_n-COOH$ wherein n represents an integer of 1 to 20. n is preferably 1 to 10, more preferably 1 to 6.

Specifically, the hydroxyalkyl group having 1 to 20 carbon atoms is $-(CH_2)_n-OH$ wherein n represents an integer of 1 to 20. n is preferably 1 to 10, more preferably 1 to 6.

The weight average molecular weight or number average molecular weight of polyallylamine is a value determined by gel permeation chromatography (GPC) measurement in terms of polyethylene oxide. More specifically, measurement of the weight average molecular weight or number average molecular weight is performed using GPC under the conditions described below.

Apparatus: HLC-8320GPC manufactured by TOSOH CORPORATION

Column: TSK-GEL G5000PWXL manufactured by TOSOH CORPORATION

Column temperature: 40° C.

Flow rate: 1.0 mL/min

Calibration curve: TOSOH TSKstandard POLY(ETHYLENE OXIDE)

Eluent: solution obtained by diluting 42.5 g of sodium nitrate to 5000 g with a mixture of water/acetonitrile (9/1)

The therapeutic agent for hyperphosphatemia of the present invention comprises, as an active ingredient, a particle (hereinafter referred to as crosslinked polymer particle) comprising a crosslinked polymer having at least a repeating unit A represented by the following formula (1-1) or (1-2) and a repeating unit B represented by the following formula (2-1) or (2-2).

[Formula 2]

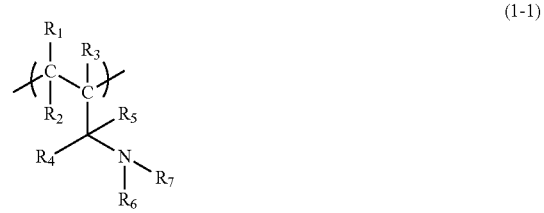

(1-1)

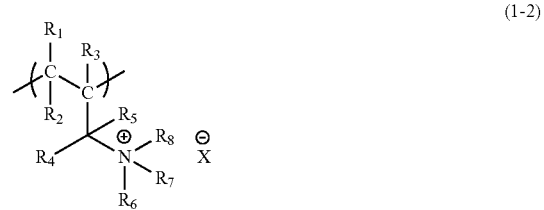

(1-2)

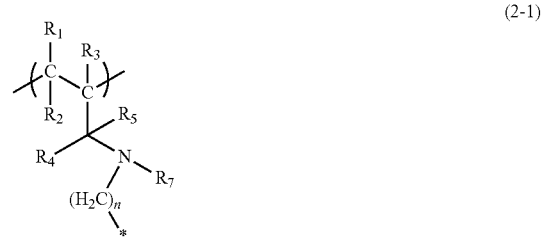

(2-1)

-continued

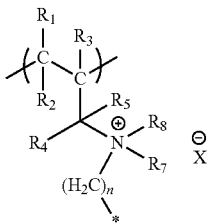

(2-2)

wherein:

$R_1$, $R_2$, $R_3$, $R_4$ and $R_5$ each independently represent a hydrogen atom, a halogen atom, or an alkyl group having 1 to 20 carbon atoms;

$R_6$, $R_7$ and $R_8$ each independently represent a hydrogen atom, an alkyl group having 1 to 20 carbon atoms, an aminoalkyl group having 1 to 20 carbon atoms or a salt thereof, an alkylaminoalkyl group having 2 to 20 carbon atoms or a salt thereof, a dialkylaminoalkyl group having 3 to 20 carbon atoms or a salt thereof, a trialkylammoniumalkyl group having 4 to 20 carbon atoms, an alkylcarbonyl group having 1 to 20 carbon atoms, a carboxyalkyl group having 1 to 20 carbon atoms, or a hydroxyalkyl group having 1 to 20 carbon atoms;

$X^-$ is a negatively charged counter ion, n represents an integer of 5 to 7, symbol * denotes a bond with a nitrogen atom on the side chain of the repeating unit A.

$X^-$ is a negatively charged counter ion, and represents $F^-$, $Cl^-$, $Br^-$, $I^-$, $PO_4^{3-}$, $PO_3^{3-}$, $CO_3^{2-}$, $HCO_3^-$, $SO_4^{2-}$, $HSO_4^-$, $OH^-$, $NO_3^-$, $S_2O_8^{2-}$, $SO_3^{2-}$, $CH_3CO_2^-$ or the like. $X^-$ is especially preferably $Cl^-$, $CO_3^{2-}$ or $HCO_3^-$.

n is more preferably an integer of 6 to 7, and is especially preferably 6.

$R_1$, $R_2$, $R_3$, $R_4$ and $R_5$ are each independently preferably a hydrogen atom, or an alkyl group having 1 to 20 carbon atoms, especially preferably a hydrogen atom.

$R_6$, $R_7$ and $R_8$ are each independently preferably a hydrogen atom, or an alkyl group having 1 to 20 carbon atoms, especially preferably a hydrogen atom.

The content of the repeating unit A in all the crosslinked polymers is preferably 90 to 99% by mole, and the content of the repeating unit B in all the crosslinked polymers is preferably 1 to 10% by mole.

The upper limit of the average particle diameter of the crosslinked polymer particles according to the present invention when the particles are dispersed in water is preferably 200 μm, more preferably 150 μm, still more preferably 120 μm, even more preferably 100 μm, especially preferably 80 μm. The lower limit of the average particle diameter is preferably 10 μm, more preferably 20 μm, still more preferably 30 μm, especially preferably 40 μm, most preferably 50 μm. The average particle diameter is preferably 10 to 200 μm, more preferably 20 to 150 μm, still more preferably 30 to 120 μm, especially preferably 40 to 120 μm, most preferably 50 to 120 μm. When the average particle diameter falls within such a numerical range, a higher effect of reducing the serum phosphorus concentration tends to be developed.

The upper limit of the swelling rate of the crosslinked polymer particles according to the present invention is preferably 20 mL/g, more preferably 16 mL/g, still more preferably 14 mL/g. The lower limit of the swelling rate is preferably 8 mL/g, more preferably 9 mL/g, still more preferably 10 mL/g. The swelling rate is preferably 8 to 20 mL/g, more preferably 9 to 16 mL/g, still more preferably 10 to 14 mL/g. When the swelling rate falls within such a numerical range, a higher effect of reducing the serum phosphorus concentration tends to be developed.

The upper limit of the circularity of the crosslinked polymer particles according to the present invention is 1. The lower limit of the circularity is preferably 0.80, more preferably 0.90. When the circularity falls within such a numerical range, a higher effect of reducing the serum phosphorus concentration tends to be developed. The circularity can be calculated as an average for 50 or more imaged particles dispersed in water in an optical microscope photograph. From the results of observation with an optical microscope, it has been determined that a particle having a circularity closer to 1 is closer to spherical form. It can be determined that as the average for 50 or more imaged particles dispersed in water becomes closer to 1, the content of crosslinked polymer particles that are not spherical decreases, and the content of global crosslinked polymer increases.

Physical properties such as the average particle diameter, swelling rate and circularity can be measured by methods similar to the methods described in examples.

The crosslinked polymer particle according to the present invention has a sparse and dense structure in which the particle has an outer shell part and a central part, and the crosslinked polymer abundance at the central part is smaller than the crosslinked polymer abundance at the outer shell part. The crosslinked polymer particle according to the present invention has an outer shell part and a central part, and the degree of crosslinking at the central part is lower than the degree of crosslinking at the outer shell part. The degree of crosslinking is a content ratio of a repeating unit having a crosslinked structure in a crosslinked polymer. In the case of a crosslinked polymer having at least a repeating unit A and a repeating unit B, the degree of crosslinking is a content ratio of the repeating unit B.

The sparse and dense structure of the crosslinked polymer can be evaluated by freeze-drying a swollen particle, and observing a scanning electron microscope image of a cross-section of the particle. The particle according to the present invention has a two-layer structure in the scanning electron microscope image. The outer shell part has no pores, and therefore appears black, and the inside part has a large number of pores, and therefore appears white. The region having no pores is a region where the crosslinked polymer abundance is high, and the region having a large number of pores is a region where the crosslinked polymer abundance is low. The region having no pores is a region where the degree of crosslinking is high, and the region having a large number of pores is a region where the degree of crosslinking is low.

It is supposed that the region having no pores is hardly swollen because the degree of crosslinking is high, and even in a swollen particle, the crosslinked polymer abundance is high. On the other hand, it is supposed that the region having a large number of pores is easily swollen because the degree of crosslinking is low, and when a swollen particle is freeze-dried, a large number of pores are formed in the swollen region of the particle, leading to a decrease in crosslinked polymer abundance.

The proportion of molecular regions which are different in movability in a swollen crosslinked body in the particle according to the present invention can be determined by pulse NMR measurement (pulse nuclear magnetic resonance measurement). Generally, in a polymer particle, a part restrained from moving, such as a crosslinked part, is attenuated at a high rate, and has a short relaxation time. That is, it is possible to discriminate the following molecular regions and calculate the proportion of the molecular regions: a molecular region (restrained part) which is near a crosslinking point, where molecular movability is considerably reduced; a molecular region (non-restrained part) which is far from the crosslinking point, where molecules can freely move; and a molecular region (semi-restrained part) which is a middle region between the restrained part and the non-restrained part, where the influence of restraint by crosslinking is small, but spatial restraint by the outer shell part limits molecular movement.

The principles and applications of pulse NMR are well known, and can be learned from, for example, Polymer, 31 (1982), p 993-997, Materials Life, Vol. 3, No. 1, p 40-47 (1991).

In pulse NMR measurement, first a measurement sample is prepared. For example, 5 mL of heavy water (manufactured by CIL (Cambridge Isotope Laboratories, Inc.)) is added to 100 mg of particles, the resulting mixture is shaken for 1 minute to uniformly disperse the particles, and then centrifugally settled, and decantation of the supernatant is performed to obtain particles swollen with heavy water. For the obtained particles, an operation of mixing heavy water and performing decantation in the same manner as described above is repeated three times to obtain heavy water-swollen particles for measurement (measurement sample).

In pulse NMR measurement, a macroscopic magnetization relaxation behavior after application of a high frequency pulse magnetic field to the measurement sample is measured to obtain a free induction attenuation signal (abscissa: time (milliseconds), ordinate: free induction attenuation signal) as shown in FIG. 11. The initial value of the obtained free induction attenuation signal is proportional to the number of protons in the measurement sample, and when the measurement sample has three components, the free induction attenuation signal appears as a sum of response signals of the three components. On the other hand, since the molecular regions included in the measurement sample (measurement particle) are different in movability, the molecular regions have different response signal attenuation rates, and are different in spin-spin relaxation time T2. Thus, the measurement sample can be divided into three components by a least-square method. The three components are defined, respectively, as a non-restrained part (Soft), a semi-restrained part (Mid) and a restrained part (Hard) in the descending order in terms of spin-spin relaxation time T2 (see FIG. 11). Here, the spin-spin relaxation time of the non-restrained part (Soft) is 2.3 milliseconds or more, the spin-spin relaxation time of the semi-restrained part (Mid) is 0.4 to 2.2 milliseconds, and the spin-spin relaxation time of the restrained part (Hard) is 0.3 milliseconds or less.

The upper limit of the proportion of the restrained part, which is required in pulse NMR, in the particles according to the present invention is preferably 70%, more preferably 65%, still more preferably 64%, even more preferably 60%, furthermore preferably 55%, especially preferably 52%. The lower limit of the proportion of the restrained part is preferably 30%, more preferably 35%, still more preferably 37%, especially preferably 40%. The proportion of the restrained part is preferably 30 to 70%, more preferably 30 to 65%, still more preferably 30 to 60%, even more preferably 35 to 55%, especially preferably 37 to 52%. When the proportion of the restrained part falls within such a numerical range, a higher effect of reducing the serum phosphorus concentration tends to be developed.

The upper limit of the proportion of the semi-restrained part, which is required in pulse NMR, in the particles according to the present invention is preferably 70%, more preferably 60%, still more preferably 55%, even more preferably 50%, especially preferably 45%. The lower limit of the proportion of the semi-restrained part is preferably 25%, more preferably 30%, still more preferably 34%, especially preferably 43%. The proportion of the semi-restrained part is preferably 25 to 70%, more preferably 25 to 60%, still more preferably 30 to 50%, even more preferably 30 to 45%, furthermore preferably 34 to 45%. When the proportion of the semi-restrained part falls within such a numerical range, a higher effect of reducing the serum phosphorus concentration tends to be developed.

The proportion of the non-restrained part, which is required in pulse NMR, in the particles according to the present invention is a balance after subtraction of the sum of the restrained part and the semi-restrained part. The upper limit of the proportion of the non-restrained part, which is required in pulse NMR, in the particles according to the present invention is preferably 25%, more preferably 20%, still more preferably 15%, especially preferably 10%. The proportion of the non-restrained part is preferably 0 to 25%, more preferably 0 to 20%, still more preferably 0 to 15%, furthermore preferably 0 to 10%. When the proportion of the non-restrained part falls within such a numerical range, a higher effect of reducing the serum phosphorus concentration tends to be developed.

The upper limit of the amine value of the particles according to the present invention is preferably 17.5 mmol/g, more preferably 17.0 mmol/g. The lower limit of the amine value is preferably 11.0 mmol/g, more preferably 12.0 mmol/g, still more preferably 13.0 mmol/g, especially preferably 14.0 mmol/g. The amine value is preferably 11.0 to 17.5 mmol/g, more preferably 12.0 to 17.5 mmol/g, still more preferably 13.0 to 17.0 mmol/g, especially preferably 14.0 to 17.0 mmol/g. When the amine value falls within such a numerical range, a higher effect of reducing the serum phosphorus concentration tends to be developed. The amine value of a nitrogen atom-containing polymer or a salt thereof represents an amine value per 1 g of solid content, which is a value obtained by determining a titer by a potentiometric titration method using a 0.1 mol/L hydrochloric acid aqueous solution, and then converting the titer to an equivalent of potassium hydroxide.

The lower limit of the phosphoric acid adsorption capacity of the particles according to the present invention is preferably 6.0 mmol/g, more preferably 6.5 mmol/g, still more preferably 7.0 mmol/g. The upper limit of the phosphoric acid adsorption capacity is practically 9.5 mmol/g, more practically 9.0 mmol/g. The phosphoric acid adsorption capacity is preferably 6.0 to 10.0 mmol/g, more preferably 6.5 to 10.0 mmol/g, still more preferably 7.0 to 10.0 mmol/g. When the phosphoric acid adsorption capacity falls within such a numerical range, a higher effect of reducing the serum phosphorus concentration tends to be developed. The phosphoric acid adsorption capacity represents an amount of phosphoric acid adsorbed per 1 g of solid content in an in vitro phosphoric acid adsorption test.

Preferably, the particles in the present invention have one or more of the following characteristics:

(a) when the free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the proportion of the semi-restrained part is 25 to 70%;

(b) when the free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the proportion of the restrained part is 30 to 70%;

(c) the phosphoric acid adsorption capacity is 6.0 to 10.0 mmol/g; and (d) the amine value is 11.0 to 17.5 mmol/g.

Specific examples of one or more of characteristics (a) to (d) include characteristic (a); characteristic (b); characteristic (c); characteristic (d); a combination of characteristics (a) and (b); a combination of characteristics (a) and (c); a combination of characteristics (a) and (d); a combination of characteristics (b) and (c); a combination of characteristics (b) and (d); a combination of characteristics (c) and (d); a combination of characteristics (a), (b) and (c); a combination of characteristics (a), (b) and (d); a combination of characteristics (a), (c) and (d); a combination of characteristics (b), (c) and (d); and a combination of characteristics (a), (b), (c) and (d).

The therapeutic agent for hyperphosphatemia according to the present invention may partly contain, in addition to the particles having a predetermined shape, crosslinked polymer-containing particles having a shape other than the predetermined shape and crushed crosslinked polymer-containing particles. The crosslinked polymer particle according to the present contain the crosslinked polymer particle according to the present invention in an amount of preferably 50% by mass or more, more preferably 70% by mass or more, still more preferably 90% by mass or more, especially preferably 95% by mass or more based on the total amount of the crosslinked polymer particle.

The therapeutic agent for hyperphosphatemia according to the present invention exhibits an effect of inhibiting absorption of phosphorus (including phosphoric acid, phosphate ions and the like), and is particularly suitable for CKD patients and dialysis patients who suffer from hyperphosphatemia. Phosphorus contained in food is absorbed at an intestinal tract, and excess phosphorus is excreted in the urine in healthy humans, but causes hyperphosphatemia in the above-mentioned patients because excretion of phosphorus is hindered due to abolition of the renal function. Hyperphosphatemia not only increases a blood calcium-phosphorus product, resulting in cardiovascular or periarticular ectopic calcification, but also causes secondary hyperparathyroidism, and is involved in various complications which lead to a reduction in vital prognosis and QOL of patients, and a reduction in ADL (activity of daily life). However, only removal of phosphorus by dialysis and restriction on intake of phosphorus by dietetic therapy are insufficient for rectification of excess phosphorus, and therefore administration of an excellent phosphorus adsorbent is needed.

(Method for Producing Crosslinked Polymer Particles)

It is preferable that the crosslinked polymer particles (preferably crosslinked polyallylamine particles) according to the present invention are produced through an emulsion preparing step of preparing an emulsion of a polymer, and a crosslinking step of carrying out a crosslinking reaction by adding a crosslinking agent to the emulsion of a polymer. The emulsion preparing step and the crosslinking step may be carried out successively, or carried out as independent steps with a predetermined time provided between the steps.

The emulsion preparing step is preferably a step of preparing an emulsion of a polymer by mixing and stirring a first solution containing a polymer and a hydrophilic solvent and having a viscosity of 10 to 2000 mPa·s and a second solution containing a hydrophobic solvent and having a viscosity of 1 to 100 mPa·s. Here, the ratio of the viscosity of the first solution to the viscosity of the second solution is preferably within a range of 0.1:1 to 300:1.

With sorbitan sesquioleate used as an emulsifier in an example in Patent Literature 8, polyallylamine particles are hardly emulsified. Thus, an emulsification operation at a high revolving speed of 600 rotations per minute is needed. Patent Literature 8 does not suggest that a polyallylamine emulsion having a small degree of variance in emulsion particle diameter can be produced with a configuration in which the viscosity of the first solution is 10 to 2000 mPa·s, the viscosity of the second solution is 1 to 100 mPa·s, and the ratio of the viscosity of the first solution to the viscosity of the second solution is within a range of 0.1:1 to 300:1. More specifically, in Patent Literature 8, since sorbitan sesquioleate is used for the second solution, the viscosity of the second solution is less than 1 mPa·s, and the viscosity ratio is not within the above-mentioned range. In the emulsion preparing step in the present invention, a polyallylamine emulsion having a small degree of variance in emulsion particle diameter can be produced by employing a configuration in which the viscosity of the first solution is 10 to 2000 mPa·s, the viscosity of the second solution is 1 to 100 mPa·s, and the ratio of the viscosity of the first solution to the viscosity of the second solution is within a range of 0.1:1 to 300:1.

[First Solution]

In the emulsion preparing step, the first solution containing a polymer having a repeating unit A represented by the above formula (1-1) or (1-2), and a hydrophilic solvent is used.

The polymer having a repeating unit represented by the formula (1-1) or the formula (1-2) (hereinafter referred to as polymer A) may contain both a repeating unit represented by the formula (1-1) and a repeating unit represented by the formula (1-2).

The preferred range of $R_1$ to $R_8$ in the formulae (1-1) and (1-2) is the same as described above, with a hydrogen atom being preferable from the viewpoint of availability of a raw material.

The polymer A may contain, in addition to the repeating units represented by the formula (1-1) and the formula (1-2), other repeating units as copolymerization components.

Examples of the salt of polymer A include halogenated hydroacid salts (e.g. hydrochlorides), phosphates, phosphites, carbonates, hydrogencarbonates, sulfates, hydrogensulfates, hydroxides, nitrates, persulfates, sulfites, acetates, ascorbates, citrates, oxalates, succinates, tartrates, taurocholates and cholates. Among them, hydrochlorides and carbonates are preferable.

Preferably, more than 0% and 50% or less of all amino groups in the polymer are neutralized in the salt of polymer A.

The polymer A or a salt thereof is preferably the polymer A or a carbonate thereof.

The lower limit of the weight average molecular weight of the polymer A is not particularly limited, but is generally 1000 or more, preferably 2000 or more, more preferably 3000 or more, and may be 5000 or more, 10,0000 or more, or 15,000 or more. The upper limit of the weight average molecular weight of the polymer A is not particularly limited, but is generally 1,000,000 or less, preferably 500,000 or less, more preferably 100,000 or less.

The polymer A is especially preferably polyallylamine. As polyallylamine, a commercialized product can be used, and examples thereof include PAA-01, PAA-03, PAA-05, PAA-08, PAA-15, PAA-15C, PAA-25, PAA-H-10C, PAA-1112, PAA-U5000 (each manufactured by NITTOBO MEDICAL CO., LTD.).

The hydrophilic solvent is not particularly limited as long as it is capable of dissolving the polymer A. The hydrophilic solvent may be water, an organic solvent or a mixture of water and an organic solvent. As the organic solvent, a lower alcohol (e.g. methanol, ethanol, n-propanol or isopropanol), acetone, acetonitrile or the like can be used. The hydrophilic solvent is preferably water.

The viscosity of the first solution is 10 to 2000 mPa·s, preferably 10 to 1500 mPa·s, still more preferably 15 to 1000 mPa·s.

The viscosity of the first solution is measured at 25° C. The viscosity can be measured by a known method. The viscosity can be measured by, for example, R215 Viscometer (RE-215L) manufactured by TOKI SANGYO CO., LTD. When the viscosity is more than 100 mPa·s, the viscosity is measured with a sample amount of 0.6 mL using a cone rotor for high viscosity (3°×R9.7). When the viscosity is 100 mPa·s or less, the viscosity is measured with a sample amount of 0.2 mL using a cone rotor for low viscosity (0.8°×R24). The revolving speed is set so that the torque value (TQ) is stable in a range of 50 to 100%, and the viscosity is read.

The content of the polymer A in the first solution is not particularly limited, but the upper limit of the content is 80% by mass, preferably 60% by mass, more preferably 50% by mass, especially preferably 40% by mass. The lower limit of the content is 1% by mass, preferably 5% by mass, more preferably 10% by mass, especially preferably 15% by mass. The content is in a range of 1 to 80% by mass, preferably 5 to 60% by mass, more preferably 10 to 50% by mass, especially preferably 15 to 40% by mass.

[Second Solution]

In the emulsion preparing step, the second solution containing a hydrophobic solvent and having a viscosity of 1 to 100 mPa·s is used.

The hydrophobic solvent is not particularly limited, and examples thereof include aromatic hydrocarbon-based solvents (e.g. benzene, toluene, xylene, mesitylene, ethylbenzene, diethylbenzene, propylbenzene, chlorobenzene, o-dichlorobenzene and t-butylbenzene), ester-based solvents (e.g. ethyl acetate, butyl acetate and propylene glycol monomethyl ether acetate), ketone-based solvents (e.g. cyclohexanone), halogen-based solvents (e.g. methylene chloride, chloroform, bromoform and carbon tetrachloride), saturated hydrocarbon-based solvents (e.g. liquid paraffin, hexane, heptane and cyclohexane), mineral oil and olive oil. These solvents may be used singly, or as a mixture of two or more thereof. The hydrophobic solvent is preferably an aromatic hydrocarbon-based solvent, an ester-based solvent or olive oil, more preferably an aromatic hydrocarbon-based solvent, especially preferably toluene or xylene.

The second solution may contain, in addition to a hydrophobic solvent, a solvent other than a hydrophobic solvent. As the solvent other than a hydrophobic solvent, a hydrophilic solvent such as an alcohol (e.g. methanol, ethanol, 2-propanol, hexanol, ethylene glycol monopropyl ether or polyethylene glycol), an ether (e.g. bis[2-methoxyethoxyethyl] or dibutyl ether), tetrahydrofuran or acetonitrile may be used. The hydrophilic solvent is preferably an alcohol or an ether, more preferably an alcohol, most preferably ethanol.

When the second solution contains a solvent other than a hydrophobic solvent, the content of the solvent other than a hydrophobic solvent is 50% or less, preferably 30% or less, more preferably 20% or less, still more preferably 15% or less in terms of a mass ratio to the content of the hydrophobic solvent. The lower limit of the content is 0.1%.

The viscosity of the second solution is 1 to 100 mPa·s. When the viscosity of the second solution is within the above-mentioned range, it is possible to prepare an emulsion of polymer A which has a small degree of variance in emulsion particle diameter. The viscosity of the second solution is preferably 2 to 60 mPa·s, more preferably 3 to 30 mPa·s.

When the second solution contains a hydrophilic solvent, the viscosity of the second solution is preferably 1 to 50 mPa·s, more preferably 1 to 30 mPa·s, still more preferably 1 to 20 mPa·s.

The viscosity of the second solution can be measured by the same method as in measurement of the viscosity of the first solution.

The ratio of the viscosity of the first solution to the viscosity of the second solution is within a range of 0.1:1 to 300:1, preferably within a range of 0.2:1 to 100:1, more preferably within a range of 0.5:1 to 50:1, especially preferably 0.9:1 to 30:1.

The second solution may be composed only of a hydrophobic solvent when the hydrophobic solvent itself, which is used in the second solution, has a viscosity of 1 to 100 mPa·s, but the second solution may contain an emulsifier for achieving a viscosity of 1 to 100 mPa·s.

Preferably, an emulsifier having a weight average molecular weight or number average molecular weight of 2000 or more is used as the emulsifier. By using an emulsifier having a weight average molecular weight or number average molecular weight of 2000 or more, a favorable emulsifying property can be achieved. The weight average molecular weight or number average molecular weight is more preferably 10,000 or more, still more preferably 50,000 or more, especially preferably 100,000 or more. The upper limit of the weight average molecular weight or number average molecular weight of the emulsifier is not particularly limited, but is generally 1,000,000 or less. The emulsifier is preferably a hydrophobic polymer.

Specific examples of the emulsifier may include:

polystyrene derivatives such as polystyrene, polyhydroxystyrene, polystyrenesulfonic acid, vinylphenol-(meth)acrylic acid ester copolymers, styrene-(meth)acrylic acid ester copolymers and styrene-vinylphenol-(meth)acrylic acid ester copolymers;

poly(meth)acrylic acid derivatives such as poly(meth)acrylic acid ester copolymers, polymethyl (meth)acrylate, poly(meth)acrylamide, polyacrylonitrile, polyethyl (meth)acrylate and polybutyl (meth)acrylate;

polyvinyl alkyl ether derivatives such as polymethyl vinyl ether, polyethyl vinyl ether, polybutyl vinyl ether and polyisobutyl vinyl ether;

polyalkylene glycol derivatives such as polypropylene glycol;

cellulose derivatives (saccharides) such as cellulose, ethyl cellulose, cellulose propionate, cellulose acetate propionate, cellulose acetate, cellulose butylate, cellulose acetate butylate, cellulose phthalate and cellulose nitrate;

polyvinyl acetate derivatives such as polyvinyl butyral, polyvinyl formal and polyvinyl acetate;

nitrogen-containing polymer derivatives such as polyvinyl pyridine, polyvinyl pyrrolidone and poly-2-methyl-2-oxazoline;

polyvinyl halide derivatives such as polyvinyl chloride and polyvinylidene chloride;

polysiloxane derivatives such as polydimethylsiloxane; and various emulsifiers such as carbodiimide resins, epoxy resins, phenol resins, melamine resins, urea resins, urethane resins, polyethylene, polypropylene, polyamide, polyimide, polycarbonate, liquid crystal polymers, polyethylene terephthalate and polybutylene terephthalate. These emulsifiers can be used singly, or in combination of two or more thereof.

As the emulsifier, saccharides such as cellulose derivatives are preferable, cellulose derivatives are more preferable, cellulose ethers such as ethyl cellulose are especially preferable, among the emulsifiers described above.

When the emulsifier is used, the used amount of the emulsifier may be an amount which makes it possible to achieve a desired viscosity for the second solution. The content of the emulsifier in the second solution is not particularly limited.

The upper limit of the content of the emulsifier in the second solution is preferably 30% by mass, more preferably 20% by mass, still more preferably 10% by mass, even more preferably 7% by mass. The lower limit of the content of the emulsifier in the second solution is preferably 0.1% by mass, more preferably 0.2% by mass, still more preferably 0.3% by mass, even more preferably 0.5% by mass.

The content of the emulsifier in the second solution is preferably 0.1 to 20% by mass, more preferably 0.1 to 10% by mass, still more preferably 0.2 to 7% by mass, even more preferably 0.3 to 5% by mass, especially preferably 0.4 to 3% by mass.

When the emulsifier is used, the second solution can be prepared by dissolving the emulsifier in the hydrophobic solvent.

[Mixing and Stirring of First Solution and Second Solution]

In the emulsion preparing step, the first solution and the second solution are mixed to obtain an emulsion of polymer A. Preferably, the mixed solution is stirred at 20 to 500 rotations per minute. In the emulsion preparing step, an emulsion of polymer A, which has high emulsion stability and a small degree of variance in emulsion particle diameter, can be produced even at such a low revolving speed by using the first solution and second solution specified above.

The mass ratio of the amounts of the first solution and the second solution used is not particularly limited, but the mass ratio of the used amount of the first solution to the used amount of the second solution is generally within a range of 5:1 to 1:10, preferably within a range of 2:1 to 1:10, more preferably within a range of 1:1 to 1:10, still more preferably within a range of 1:1 to 1:5, especially preferably within a range of 1:1 to 1:3.

Mixing of the first solution and the second solution can be performed in a container such as a beaker. Preferably, the mixed solution obtained as described above is stirred at 20 to 500 rotations per minute. The containers that are used for mixing and stirring may be the same or different.

The capacity of the container that is used for stirring is not particularly limited, but is generally within a range of 100 mL to 100,000 L.

The temperature at which stirring is performed is not particularly limited, but is generally 2° C. to 98° C., preferably 5° C. to 80° C., more preferably 10° C. to 70° C.

The stirring speed is preferably 20 to 500 rotations per minute, more preferably 30 to 400 rotations per minute, still more preferably 40 to 300 rotations per minute, especially preferably 50 to 300 rotations per minute.

Stirring can be performed by a common method using, for example, a stirring blade and a motor. The size of the stirring blade can be appropriately set according to the capacity of a container to be used. As one example, when the mixed solution is stirred in a 500 mL flask, a stirring blade having a blade diameter of about 40 mm to 100 mm can be used.

For the ratio of the maximum inner diameter of the container and the length of the stirring blade, the ratio of the length of the stirring blade to the maximum inner diameter of the container (diameter in the case of a cylindrical container) is preferably 3/10 or more and less than 1, more preferably 5/10 or more and 9/10 or less.

Even when the capacity of the container is changed, stirring conditions can be adjusted by the number of rotations. Preferably, stirring conditions are optimized by adjusting the size or shape of the stirring blade and the number of rotations. Preferably, the number of rotations is adjusted according to the size and shape of the stirring blade, for example, a smaller number of rotations is set when the stirring blade has a large size, and a larger number of rotations is set when the stirring blade has a small size.

The stirring time is not particularly limited, and can be appropriately set according to the capacity of the container, or the like, but is generally 1 minute to 10 hours, preferably 5 minutes to 5 hours, more preferably 10 minutes to 3 hours, still more preferably 15 minutes to 2 hours.

The average emulsion particle diameter of the emulsion of polymer A, which is obtained by stirring described above, is not particularly limited, but the preferred average emulsion particle diameter corresponds to a preferred range of diameters of particles.

The average emulsion particle diameter can be measured by a known method, and for example, the following method can be used. An emulsion of a polymer, which is obtained by stirring, is left standing for 1 hour, and then added dropwise into dry ice methanol at −78° C. to solidify particles of the polymer. An optical microscope photograph of 1000 or more randomly selected frozen particles is stored as electronic data, and the average particle diameter of the frozen particles is calculated using Software ImageJ made by National Institutes of Health.

[Crosslinking Step]

The crosslinking step may include (1) adding a crosslinking agent to an emulsion of polymer A to carry out a crosslinking reaction or (2) mixing a crosslinking agent with the second solution, then mixing the first solution with the second solution, and emulsifying the resulting mixture to carry out a crosslinking reaction, but is not particularly limited.

The reaction time in the crosslinking step is preferably 1 to 36 hours, more preferably 3 to 24 hours, especially preferably 6 to 20 hours.

From the viewpoint of a high reaction rate, the crosslinking step is desirable to include causing the crosslinking reaction to proceed after removing water in the first solution. Thus, it is preferable to carry out the crosslinking reaction at a temperature of 95° C. or higher using a Dean-Stark tube or the like.

That is, it is preferable to carry out the reaction for 1 to 24 hours after completion of removal of water by distillation. The reaction time is more preferably 2 to 20 hours, especially preferably 3 to 16 hours.

The crosslinking agent is preferably an alkylene type crosslinking agents having 5 to 7 carbon atoms. More specifically, examples of the crosslinking agent includes 1,5-dichloropentane, 1,5-dibromopentane, 1,6-dichlorohexane, 1,6-dibromohexane, 1,6-bis(para-toluenesulfonyl)hexane, 1,7-dichloroheptane, and 1,7-dibromoheptane. Among them, dihalohexane is preferred. 1,6-dibromohexane or 1,6-dichlorohexane is more preferred, and 1,6-dichlorohexane is especially preferred. By using such a hydrophobic crosslinking agent, a higher effect of reducing the serum phosphorus concentration tends to be developed. The crosslinking agent is preferably used in an amount such that the content of the repeating unit B is 1 to 10% by mole, more preferably 1.25 to 8% by mole, and still more preferably 1.5 to 6% by mole.

In the crosslinking step, the crosslinking agent is diluted with a predetermined solvent to obtain a solution, and the crosslinking agent solution is used. As the solvent, a solvent that is the same as any of the hydrophobic solvents described above can be used. The solvent is preferably an aromatic hydrocarbon-based solvent, especially preferably toluene.

In the case of the method (1), a crosslinking agent solution is added dropwise to an emulsion of polymer A over 0 to 240 minutes, and subsequently, the resulting mixture is reacted at 40 to 140° C. for 1 to 36 hours. The reaction time is preferably 1 to 36 hours, more preferably 1 to 24 hours, especially preferably 6 to 20 hours.

Subsequently, the particles are washed with a predetermined solution, and filtered, the resulting particles are dried to obtain particles according to the present invention. The resulting particles contain a crosslinked polymer A having at least a repeating unit A represented by the above formula (1-1) or (1-2) and a repeating unit B represented by the above formula (2-1) or (2-2).

The particles according to the present invention may be obtained through a crosslinking reaction carried out by adding a crosslinking agent to an emulsion obtained by emulsifying the polymer A or a salt thereof as described above. More specifically, the particles are obtained through a crosslinking reaction carried out by adding a crosslinking agent to an emulsion obtained by emulsifying the polymer A or a salt thereof, the emulsion is obtained by mixing a first solution containing the polymer A or a salt thereof and a hydrophilic solvent and having a viscosity of 10 to 2000 mPa·s and a second solution containing a hydrophobic solvent and having a viscosity of 1 to 100 mPa·s, and the ratio of the viscosity of the first solution to the viscosity of the second solution is preferably within a range of 0.1:1 to 300:1. Preferably, the second solution contains an emulsifier having a weight average molecular weight or number average molecular weight of 2000 or more. The emulsifier is preferably a saccharide, especially preferably cellulose ether.

The particles according to the present invention are preferably spherical, and when swollen, the particles develop a core-shell structure, which has been found to have a high degree of crosslinking and a dense-polymer structure at the outside and a low degree of crosslinking and a sparse-polymer structure at the inside. The outside shell layer has an effect of improving phosphorus permselectivity of competitive adsorbing substances present in the body. It is thought that the inside core layer has flexible movability, so that phosphorus can be adsorbed with high efficiency, leading to improvement of the phosphorus adsorption capacity. It is thought that in the particles according to the present invention, the ratio of the inside core layer can be set to a desired ratio in the above-described production method, so that phosphorus can be adsorbed with high efficiency. The proportion of the inside core layer is assumed to be reflected in the proportion of the semi-restrained part which is obtained by pulse NMR measurement of the particles.

Bixalomer is spherical, but does not develop a core-shell structure.

The particle which contains the crosslinked polymer used in the present invention can be administered alone as such, but are normally desirable to be provided as various pharmaceutical preparations. Those pharmaceutical preparations are used for animals or humans, preferably for humans.

The pharmaceutical preparation according to the present invention may contain particles, which contain the crosslinked polymer as an active ingredient, alone or as a mixture with any other effective ingredient for treatment. Such a pharmaceutical preparation is produced by any method well known in the pharmaceutical technical field, where an active ingredient is mixed together with one or more pharmaceutically acceptable carriers (diluent, solvent, excipient and so on).

It is desirable to use a route of administration which is most effective in treatment, and examples thereof may include oral administration.

Examples of the dosage form include tablets.

A tablet or the like suitable for oral administration can be produced using an excipient such as lactose, a disintegrator such as starch, a lubricant such as magnesium stearate, a binding agent such as hydroxypropyl cellulose and the like.

The dosage and the number of doses of particles containing a crosslinked polymer for use in the present invention vary depending on a dosage form, a patient's age or weight, a nature or degree of seriousness of a symptom to be treated, or the like, but in the case of oral administration, the particles are normally administered in a dosage of 0.01 g to 30 g one time to several times a day per adult human. However, the dosage and the number of doses vary depending on various conditions described above.

Another aspect of the present invention provides a therapeutic method comprising a step of administering the particles or pharmaceutical preparation according to the present invention to a subject (the subject refers to mammals including humans, preferably humans, more preferably CKD patients and dialysis patients who suffer from hyperphosphatemia). The therapeutic method according to the present invention is used for treatment of hyperphosphatemia.

Another aspect of the present invention provides particles according to the present invention for use in treatment of hyperphosphatemia.

Another aspect of the present invention provides use of the particles according to the present invention for production of a therapeutic agent for hyperphosphatemia.

EXAMPLES

The present invention will be described in further detail by way of examples below, but the present invention is not limited to the examples.
[Swelling Rate of Particles]

The swelling rate was calculated by dividing the volume of particles after swelling obtained by repeating shaking and 1-hour or longer still standing 20 or more times in an aqueous solution at 20° C. containing 2.2% by mass of sodium 2-morpholinoethanesulfonate and 0.5% by mass of sodium chloride and having a pH of 6.3 by the mass of the particles before swelling.

The number of times of repeating shaking and 1-hour or longer still standing may be performed until there is no change in swelling particle volume.

More specifically, 21.7 g of sodium 2-morpholinoethanesulfonate (produced by Aldrich Japan Inc.) and 4.7 g of sodium chloride (produced by Wako Pure Chemical Corporation) were weighed in a 1-L-measuring flask and diluted to 1 L with water. The solute was dissolved completely, and 30% by mass hydrochloric acid was then added until pH reached 6.3 to prepare a buffer.

Then, 0.30 g of particles obtained in each of Examples and Comparative Examples were weighed in a 10-mL measuring cylinder and mixed with 10 mL of the buffer. The particles were homogeneously suspended by stirring for 1 minute using a spatula, and the mixture was then left to stand. The volume of the swelling particles settled was read from the scale of a measuring cylinder 24 hours after, the mixture was weakly shaken for 1 minute, and the particles were left to stand for further 24 hours. The above-mentioned shaking and standing were repeated until there was no change in the swelling particle volume. The swelling rate (mL/g) was calculated by divided the swelling particle volume when there was no change by the particle mass (0.30 g).

[Shapes of Particles]

The shapes of particles were determined from optical microscope photographs. More specifically, particles obtained in each of Examples and Comparative Examples were dispersed in water, and an optical microscope (manufactured by NIKON CORPORATION, ECLIPSE E600POL) photograph of 500 or more particles selected at random were taken. When the projected area of substantially circular particles among the projected areas of all the particles in a photograph was 60% or more, it was determined that those particles were spherical. The projected area of substantially circular particles is preferably 80% or more, more preferably 90% or more, and further preferably 95% or more. As the projected area of substantially circular particles becomes higher, it becomes more preferable.

For dispersion in water, 0.1 g of particles after drying were weighed in a sample bottle, followed by the addition of 10 mL of pure water. The mixture was shaken and mixed, and then left to stand at 25° C. for 10 minutes to prepare an aqueous dispersion.

[Average Particle Diameter of Particles]

The average particle diameter is calculated as a volume average particle diameter by converting an area of 1000 or more imaged particles dispersed in water in an optical microscope photograph to diameters and using the diameters.

More specifically, particles obtained in each of Examples and Comparative Example were dispersed in water, an optical microscope (manufactured by NIKON CORPORATION, ECLIPSE E600POL) photograph of 1000 or more particles selected at random was then taken and saved as electronic data, and the average particle diameter of the particles was calculated using the software ImageJ of U.S. National Institutes of Health.

For dispersion in water, 0.1 g of particles after drying were weighed in a sample bottle, followed by the addition of 10 mL of pure water. The mixture was shaken and mixed and then left to stand at 25° C. for 10 minutes to prepare an aqueous dispersion.

For photography through the optical microscope, reflected light was observed at a magnification of 50 times (eyepiece 10 times, objective lens 5 times). When the number of particles per photograph was less than 1000, a plurality of photographs were analyzed, and data thereof were calculated together.

Analysis processing was performed in particle analysis using ImageJ by:

(a) reading a photograph taken through the optical microscope using ImageJ;

(b) performing smoothing processing, 8-bit processing, black and white 2 coloring, fill-up processing and the division processing of binding particles; and (c) limiting the analysis range to a particle diameter of 10 μm or more and a circularity of 0.5 or more to remove noise.

[Circularity of Particles]

The circularity is the average value of the circularities: $4\pi \times (area)/(square\ of\ circumference)$ of 50 or more particle images in an optical microscope photograph. When the circularity is 1, it is shown that the particles are perfect circles.

More specifically, particles obtained in each example and each comparative were dispersed in water, an optical microscope (manufactured by NIKON CORPORATION, ECLIPSE E600POL) photograph of 50 or more particles selected at random was then taken and saved as electronic data, and the circularity of the particles was calculated using the software ImageJ of U.S. National Institutes of Health.

For dispersion in water, 0.1 g of particles after drying were weighed in a sample bottle, followed by the addition of 10 mL of pure water. The mixture was shaken and mixed, and then left to stand at 25° C. for 10 minutes to prepare an aqueous dispersion.

For photography through the optical microscope, reflected light was observed at a magnification of 50 times (eyepiece 10 times, objective lens 5 times). When the number of particles per photograph was less than 50, a plurality of photographs were analyzed, and data thereof were calculated together. Analysis processing was performed in particle analysis using ImageJ by:

(a) reading a photograph taken through the optical microscope using ImageJ;

(b) performing smoothing processing, 8-bit processing, black and white 2 coloring, and fill-up processing;

(c) excluding superimposed particles and particles which were partially shown on the edges of the photograph manually since they influenced the calculation of circularity.

(d) limiting an analysis range to a particle diameter of 10 μm or more to remove a noise.

[Viscosity Measurement]

The viscosity at 25° C. was measured with an R215 viscosity meter (RE-215L) manufactured by Toki Sangyo Co., Ltd. When the viscosity was more than 100 mPa·s, a sample was measured in an amount of 0.6 mL using a cone rotor for high viscosity (3°×R9.7). When the viscosity was 100 mPa·s or less, a sample was measured in an amount of 0.2 mL using a cone rotor for low viscosity (0.8°×R24). The rotational speed was set so that the index value (TQ) was stable in the range of 50 to 100% in any case, and the viscosity was read.

[Scanning Electron Microscopy Images of Particle Sections]

Freeze-dried particles were used for the observation of swollen particle structure. In a freeze-drying step, 20 mL of ultrapure water was mixed with 0.2 g of particles produced in each of Examples and Comparative Examples, and the mixture was shaken and mixed, and then left to stand for 1 hour to prepare an aqueous dispersion. Next, the mixture was centrifuged at 3000 G for 10 minutes, the supernatant was removed by decantation, and 20 mL of ethanol was added. This solvent replacement step was repeated 3 times to obtain particles dispersed in ethanol. Subsequently, ethanol was removing by centrifugal separation, and the solvent was then replaced with 20 mL of t-butanol. This step was repeated 3 times to obtain particles dispersed in t-butanol. The particles dispersed in t-butanol were frozen at −18° C. or less and freeze-dried by the usual method. This step was operated so that the diameter of the particles dispersed in water is substantially the same as that of the particles dispersed in t-butanol.

A section was exposed by subjecting the obtained freeze-dried particles to embedding treatment and cutting the particles by a microtome. The section was subjected to vapor deposition treatment with osmium, and the freeze-dried particle section subjected to vapor deposition treatment was measured under a scanning electron microscope equipped with an FE (Field Emission) gun at a free working distance of 8 mm and an accelerating voltage of 2 kV to acquire images. The images were acquired to select particles wherein the section passed near the center of the particles. Specifically, the images of particles having sectional diameters within ±30% of the average particle diameter were acquired. Even though particles had core-shell structure, the core-shell structure cannot be observed in the case of cutting the ends of particles. Therefore, it is necessary to select particles properly.

[Crosslinked Domain Analysis by Pulse NMR]

First, 5 mL of heavy water (produced by Cambridge Isotope Laboratories, Inc.) was added to 100 mg of particles produced by each of Examples and Comparative Examples. The mixture was shaken and mixed for 1 minute, resulting in homogeneous dispersion. The particles were then subjected to centrifugal sedimentation, followed by the removal of the supernatant by decantation to obtain particles swollen with heavy water. The obtained particles were subjected to the operation of mixing heavy water and removing it by decantation in the same way as mentioned above repeatedly 3 times to obtain particles swollen with heavy water for measurement (measurement sample). Next, the measurement sample was measured using an MQ-20 manufactured by Bruker Biospin K.K. Measurement was performed by solid echo at a 90° pulse interval of 1 microsecond, reading time of 5 milliseconds and the number of data points of 2000. The nuclide was $^1$H, the number of times of integration was 64, the repeating time was 2 seconds, and measurement was performed at 24° C. The obtained free induction decay signal was fitted by the least squares method as the sum of three components shown in expression (1). The spin-spin relaxation times $T_{2,1}$, $T_{2,2}$, and $T_{2,3}$, the intensities $A_1$, $A_2$, and $A_3$ were calculated thereby.

$$y = A_1 * \exp(-(1/(\alpha_1)(t/T_{2,1})^{\alpha_1}) + A_2 * \exp(-(1/(\alpha_2)(t/T_{2,2})^{\alpha_2}) + A_3 * \exp(-(1/(\alpha_3)(t/T_{2,3})^{\alpha_3}) \quad (1)$$

t is time, and y is the intensity of the free induction decay signal. $\alpha_1$, $\alpha_2$, and $\alpha_3$ represents shape factors. Analysis was performed by setting $\alpha_1$ and $\alpha_2$ as 1 and $\alpha_3$ as 2.

A component having low molecular mobility and short relaxation time was defined as a restrained part. A component having high molecular mobility and long relaxation time was defined as a non-restrained part. A component having middle relaxation time therebetween was defined as a semi-restrained part. The component ratios and the relaxation times were evaluated. The proportion of the restrained part, the proportion of the semi-restrained part, the proportion of the non-restrained part showed the proportions of the respective regions to the whole, and were calculated by dividing $A_1$ to $A_3$ by the total value of $A_1$ to $A_3$, respectively.

[Loss on Drying]

In the measurement of an amine value and phosphate adsorption capacity, the influence of water and the like was excluded by measuring and correcting loss on drying value separately to exclude the influence of an increase in water and the like due to elapsed time at the time of the storage of samples. As the measurement of loss on drying, a weighing bottle was first dried at 120° C. for 30 minutes and cooled to room temperature in a desiccator containing silica gel, and its weight (W1) was measured correctly. Around 100 mg of particles produced in each of Examples and Comparative Examples were taken into the weighing bottle, and the weight (W2) of the weighing bottle was measured. Next, a 50-mL vial containing around 20 g of potassium hydroxide was placed in a vacuum drier. The above-mentioned weighing bottle containing the particles was subjected to drying treatment in the same vacuum drier at 120° C. for 5 hours and then cooled to room temperature in the desiccator containing silica gel. The weight (w3) of the weighing bottle was measured. The value of loss on drying D (%) was calculated by expression (2).

$$D(\%) = (W2 - W3)/(W2 - W1) \times 100 \quad (2)$$

[Amine Value]

First, 100 mg of particles produced by each of Examples and Comparative Example were weighed in a 4-mL vial (the exact weighing value is defined as W g), a weighing bottle was dried at 120° C. for 30 minutes and cooled to room temperature in the desiccator containing silica gel. Then, 1 mL of water was added in the dry vial containing the particles, resulting in swelling. Next, 500 μL of 5 N hydrochloric acid was then added, and further 2 mL of water was added. The mixture was stirred for 30 minutes with a magnetic stirrer. Then, the contents in the 4-mL vial were poured into a 200-mL beaker, and 90 mL of ultrapure water was added. The mixture was subjected to neutralization titration with a 0.1 N sodium hydroxide aqueous solution using the potential difference automatic titrators MCU-610 and AT-610 manufactured by Kyoto Electronics Manufacturing Co., Ltd., and the titer (V mL) to neutralize was calculated. The amine value was calculated by expression (3). fHCl and fNaOH denote factor values.

$$\text{Amine value(mmol/g)} = \{(5 \times 0.5 \times f\text{HCl} - 0.1 \times V \times f\text{NaOH})/W\} \times \{100/(100-D)\} \quad (3)$$

[Phosphate Adsorption Capacity]

First, 21.72 g of sodium morpholinoethanesulfonate (produced by Aldrich Japan Inc.), 4.67 g of sodium chloride (produced by Wako Pure Chemical Corporation), and 2.88 g of 85% phosphoric acid (produced by Wako Pure Chemical Corporation) were weighed in 1-L measuring cylinder and adjusted to 1 L with ultrapure water to prepare a phosphoric acid-containing buffer at pH 6.4. Then, 30 mg (the accurate weighing value is defined as W' mg) of particles produced in each of Examples and Comparative Examples were weighed in a 20-mL container made of polyethylene terephthalate, 20 mL of the above phosphoric acid-containing buffer was mixed, and the mixture was stirred with the magnetic stirrer in a constant temperature oven at 37° C. for 1 hour. The aqueous solution before mixing with the particles and the aqueous solution after mixing with the particles and stirring were filtered through syringe filters. A phosphorus element in filtrate was quantitated by ICP emission spectrochemical analysis. The phosphate adsorption capacity was calculated by expression (4). Here, the phosphorus concentration before mixing was defined as $P_0$ ppm, and the phosphorus concentration after mixing and stirring was defined as P ppm.

$$\text{Phosphate adsorption capacity(mmol/g)} = \{(P - P_0) \times 20/(30.97 \times W')\} \times \{100/(100-D)\} \quad (4)$$

Example 1-1

Water was distilled under a reduced pressure from 400 g of a 15.0% by mass polyallylamine aqueous solution (produced by NITTOBO MEDICAL CO., LTD., PAA-15C, amine value 17.5 mmol/g) to prepare 150 g of a 40.0% by mass polyallylamine aqueous solution (a first solution).

Then, 15.0 g of ethyl cellulose (Ethyl Cellulose 45 produced by Wako Pure Chemical Corporation (around 49% ethoxy), the weight average molecular weight was 125,000) was dissolved in 303 g of toluene to prepare 318 g of a second solution.

The above-mentioned first solution and the above-mentioned second solution were mixed in a 500-mL separable flask comprising a dean-stark device to obtain a mixture. The above-mentioned mixture was stirred at 60° C. at 120 rotations/minute for 60 minutes using flat stirring blades made of stainless steel (R1375 manufactured by IKA Corporation, blade diameter 70 mm) and a Three-one motor manufactured by SHINTO Scientific Co., Ltd. (BL600) to obtain a polyallylamine emulsified liquid. The physical property of the obtained emulsified liquids is shown in Table 1. The physical property of the emulsified liquids in each of Examples and Comparative Examples is shown in Table 1. The molecular weight in Table is weight average molecular weight.

A solution obtained by diluting 4.08 g of 1,6-dichlorohexane (produced by Tokyo Chemical Industry Co., Ltd.) with 10 mL of toluene was dropped into the obtained emulsified liquid over 5 minutes. Then, 74 mL of water was removed by raising bath temperature to 120° C. after dropping and refluxing for 4 hours. The flask temperature was cooled to room temperature, and the supernatant was removed by decantation. The obtained particles were purified by repeating reslurrying with ethanol (500 mL, 3 times), 1 mol/L NaOH aqueous solution:water (60 mL:440 mL, once), water (500 mL, twice) and ethanol (500 mL, 1 time) and filtration. The obtained particles were dried at 50° C. for 48 hours with a ventilation drier and dried at 70° C. for 12 hours with a vacuum drier to obtain crosslinked polyallylamine globules. Refer to the following for the reaction formula.

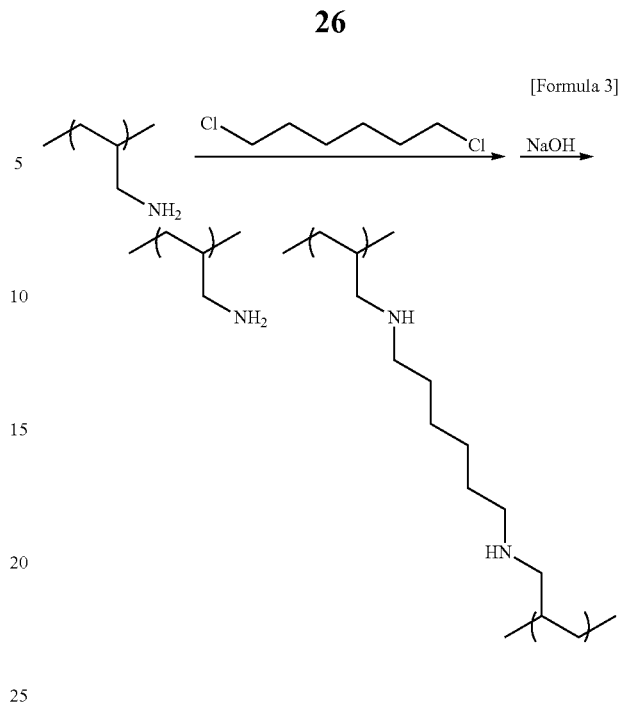

[Formula 3]

The circularity, the amount of the crosslinking agent used (ratio to all raw materials), the swelling rate, and the particle diameter of crosslinked polyallylamine globule particles in Example 1-1 are shown in Table 2. The circularity, the amount of the crosslinking agent used, the swelling rate, and the particle diameter of those in each Examples and Comparative Examples are shown in Table 2. Also, a scanning electron microscope image in Example 1-1 was shown in FIG. 1, and an optical microscope photograph in Example 1-1 was shown in FIG. 2.

The rates of the molecule regions determined by pulse NMR, the amine value and the phosphate adsorption capacity in each of Examples and Comparative Examples are shown in Table 3.

TABLE 1

| | Composition of first solution | Viscosity of first solution (mPa · s) | Hydrophobic solvent | Emulsifier | Viscosity of second solution (mPa · s) | Viscosity ratio (first solution/second solution) | Number of rotations (rotations/minute) |
|---|---|---|---|---|---|---|---|
| Example 1-1 | Aqueous 40% by mass polyallylamine (molecular weight 15000) solution | 1377 | Toluene | Ethyl cellulose (4.7% by mass) | 92 | 15 | 120 |
| Example 2 | Aqueous 40% by mass polyallylamine (molecular weight 15000) solution | 1377 | Toluene | Ethyl cellulose (4.7% by mass) | 92 | 15 | 120 |
| Example 3 | Aqueous 40% by mass polyallylamine (molecular weight 15000) solution | 1377 | Toluene | Ethyl cellulose (4.7% by mass) | 92 | 15 | 120 |

TABLE 1-continued

| | Composition of first solution | Viscosity of first solution (mPa·s) | Hydrophobic solvent | Emulsifier | Viscosity of second solution (mPa·s) | Viscosity ratio (first solution/second solution) | Number of rotations (rotations/minute) |
|---|---|---|---|---|---|---|---|
| Example 4 | Aqueous 40% by mass polyallylamine (molecular weight 15000) solution | 1377 | Toluene | Ethyl cellulose (4.7% by mass) | 92 | 15 | 120 |

TABLE 2

| | Polymer | Crosslinking agent | Circularity | Amount of crosslinking agent used (% by mass) | Swelling rate (mL/g) | Average particle diameter (µm) |
|---|---|---|---|---|---|---|
| Example 1-1 | Polyallylamine | Dichlorohexane | 0.93 | 3.6 | 12.4 | 56 |
| Example 2 | Polyallylamine | Dichlorohexane | 0.93 | 3.6 | 12.7 | 27 |
| Example 3 | Polyallylamine | Dichlorohexane | 0.91 | 3.6 | 11.7 | 113 |
| Example 4 | Polyallylamine | Dichlorohexane | 0.92 | 6.9 | 8.7 | 49 |
| Comparative Example 1 | Polyallylamine | Epichlorohydrin | 0.55 | 10 | 8.8 | 180 |
| Comparative Example 3 | N,N,N',N'-tetrakis(3-aminopropyl)butane-1,4-diamine | Epichlorohydrin | 0.92 | 26.8 | 4.3 | 100 |
| Comparative Example 5 | Polyallylamine | Epichlorohydrin | 0.70 | 9 | 9.3 | 435 |
| Comparative Example 6 | Polyallylamine | Epichlorohydrin | 0.87 | 12.5 | 5.6 | 179 |

TABLE 3

| | Amine value (mmol/g) | Phosphate adsorption capacity (mmol/g) | Restrained part (Hard) $T_{2,1}$ (ms) | $A_1$ | Ratio | Semi-restrained part (Mid) $T_{2,1}$ (ms) | $A_2$ | Ratio | Non-restrained part (Soft) $T_{2,3}$ (ms) | $A_3$ | Ratio |
|---|---|---|---|---|---|---|---|---|---|---|---|
| Example 1-1 | 14.4 | 7.5 | 0.087 | 0.44 | 49% | 1.010 | 0.39 | 43% | 2.9 | 0.07 | 8% |
| Example 2 | 15.1 | 7.3 | 0.080 | 0.48 | 52% | 0.762 | 0.32 | 34% | 2.8 | 0.13 | 14% |
| Example 3 | 16.0 | 7.7 | 0.101 | 0.35 | 38% | 1.500 | 0.42 | 45% | 2.6 | 0.16 | 17% |
| Comparative Example 1 | 8.8 | 4.1 | 0.040 | 0.55 | 57% | 1.798 | 0.22 | 23% | 3.1 | 0.20 | 21% |
| Comparative Example 3 | 10.7 | 3.9 | 0.041 | 0.87 | 79% | 0.640 | 0.14 | 13% | 3.4 | 0.09 | 8% |
| Comparative Example 5 | 9.4 | 5.6 | 0.047 | 0.72 | 71% | 1.128 | 0.16 | 16% | 3.3 | 0.13 | 13% |
| Comparative Example 6 | 8.2 | 5.4 | 0.024 | 0.62 | 59% | 1.072 | 0.13 | 12% | 3.0 | 0.30 | 29% |

Example 2

Water was distilled under a reduced pressure from 480 g of a 15.0% by mass polyallylamine aqueous solution (produced by NITTOBO MEDICAL CO., LTD., PAA-15C, amine value 17.5 mmol/g) to prepare 180 g of a 40.0% by mass polyallylamine aqueous solution (a first solution).

Then, 18.0 g of ethyl cellulose (Ethyl Cellulose 45 produced by Wako Pure Chemical Corporation (around 49% ethoxy), the weight average molecular weight was 125,000) was dissolved in 364 g of toluene to prepare 382 g of a second solution.

The above-mentioned first solution and the above-mentioned second solution were mixed in a 500-mL separable flask comprising the dean-stark device to obtain a mixture. The above-mentioned mixture was stirred at 50° C. at 120 rotations/minute for 60 minutes using flat stirring blades made of stainless steel (R1375 manufactured by IKA Corporation, blade diameter 70 mm) and a Three-one motor manufactured by SHINTO Scientific Co., Ltd. (BL600) to obtain a polyallylamine emulsified liquid.

A solution obtained by diluting 4.90 g of 1,6-dichlorohexane (produced by Tokyo Chemical Industry Co., Ltd.) with 12 mL of toluene was dropped into the obtained emulsified liquid over 10 minutes. Then, 88 mL of water was removed by stirring for 2.5 hours after dropping, raising bath temperature to 120° C., refluxing for 4 hours. Crosslinked polyallylamine globules were obtained by performing the same as in Example 1-1 thereafter.

Example 3

Crosslinked polyallylamine globules were obtained in the same way as in Example 2 except that the temperature at the time of stirring was changed from 50° C. to 80° C.

Example 4

Crosslinked polyallylamine globules were obtained in the same way as in Example 2 except that the temperature at the time of stirring was changed from 50° C. to 60° C., the weight of 1,6-dichlorohexane was changed from 4.90 g to 9.79 g, and the reflux time was changed from 4 hours to 5.5 hours.

Example 1-2

First, 5 L of water was added to 248 g of crosslinked polyallylamine globules of Example 1-1, and the mixture was stirred at room temperature and 100 rotations/minute for 30 minutes. To the obtained suspension was added 173 mL of 30% by mass hydrochloric acid (produced by Wako Pure Chemical Corporation), and the mixture was stirred at room temperature at 100 rotations/minute for 1 hour. The reaction liquid was filtered and purified by repeating reslurrying and filtration with water (5 L, twice). The obtained particles were dried at 50° C. for 48 hours with a ventilation drier and dried at 70° C. for 12 hours with a vacuum drier to obtain crosslinked polyallylamine globules.

Example 1-3

First, 3 L of water was added to 150 g of crosslinked polyallylamine globules of Example 1-1, and the mixture was stirred at room temperature and 100 rotations/minute for 30 minutes. To the obtained suspension was added 105 mL of 30% by mass hydrochloric acid (produced by Wako Pure Chem, Inc.), and the mixture was stirred at room temperature and 100 rotations/minute for 1 hour. The reaction liquid was filtered and purified by repeating reslurrying with water (3 L, twice) and filtration.

Then, 3 L of water and 215 g of sodium carbonate (produced by Wako Pure Chem, Inc.) were added to the obtained particles, and the mixture was stirred at room temperature and 100 rotations/minute for 2 hours. The reaction liquid was filtered, and reslurrying with water (3 L, 4 times) and filtration were repeated, resulting in purification. The obtained particles were dried at 50° C. for 48 hours with a ventilation drier and dried at 70° C. for 12 hours with a vacuum drier to obtain crosslinked polyallylamine globules.

Preparation Example

Tablets comprising the following composition are prepared by a usual method. The crosslinked polyallylamine globules obtained in Example 1-1 (40 g), lactose (286.8 g) and potato starch (60 g) are mixed, and a 10% aqueous solution of hydroxypropyl cellulose (120 g) is added to this. This mixture is kneaded, granulated, dried, then sized and formed into granules for tablet compression by a usual method. Magnesium stearate (1.2 g) is added to this and mixed, and tablet compression is performed with a tableting machine (manufactured by KIKUSUI SEISAKUSHO LTD., RT-15) with a punch having a diameter of 8 mm to obtain tablets (containing 20 mg of an active ingredient per tablet).

| Prescription | Crosslinked polyallylamine globules obtained in Example 1-1 | 20 mg |
|---|---|---|
| | Lactose | 143.4 mg |
| | Potato starch | 30 mg |
| | Hydroxypropyl cellulose | 6 mg |
| | Magnesium stearate | 0.6 mg |
| | | 200 mg |

Comparative Examples 1 and 2

As Sevelamer hydrochloride, in Test Example 1 and Test Example 2, tablets of PHOSBLOCK® produced by Kyowa Hakko Kirin Co., Ltd. were pulverized and used as the therapeutic agents for hyperphosphatemia of the Comparative Examples. The amount equivalent to that of the corresponding example in each Test Example was administered in Comparative Example 1, and the amount which was twice as much as that of the example was administered in Comparative Example 2. In photography of a scanning electron microscope and an optical microscope, and the measurement of the swelling rate, every 1 g of tablets of PHOSBLOCK® produced by Kyowa Hakko Kirin Co., Ltd. were mixed with 50 g of ultrapure water. A crosslinked polymer corresponding to the drug substance was extracted by shaking the mixture for 1 hour or more, then filtering it and drying it and used for evaluation.

A scanning electron microscopy image of Sevelamer hydrochloride was shown in FIG. 3, and an optical microscope photograph of Sevelamer hydrochloride was shown in FIG. 4.

Comparative Examples 3 and 4

As Bixalomer, Kiklin® capsules produced by Astellas Pharma Inc. were provided, the drug substance was extracted from the capsule and used as the therapeutic agents for hyperphosphatemia of the Comparative Examples. The amount equivalent to that of the corresponding example in each Test Example was administered in Comparative Example 3, and the amount which was twice as much as that of the example was administered in Comparative Example 4. A scanning electron microscopy image of Bixalomer was shown in FIG. 5, and an optical microscope photograph of Bixalomer was shown in FIG. 6.

Comparative Example 5

Synthesis was performed based on Example 2 of Patent Literature 7.

That is, 35.6 g of a 40.0% by mass polyallylamine aqueous solution, 24.3 mL of water, 8.50 mL of 30% by mass hydrochloric acid and 10.0 g of sodium chloride were mixed at 25 to 35° C. to obtain a 22.4% by weight aqueous solution of polyallylamine hydrochloride. The solution was cooled at 5° C. to 15° C., and 200 mL of toluene and 1 g of Span 85 (sorbitan trioleate) were added. Next, the temperature of the reactive mixture was raised to 20° C. to 25° C. and maintained at 250 rotations/minute for 15 minutes. The reaction mixture was filtered at 25 to 35° C., and all foreign substances were removed.

The filtrate was poured into a 500-mL separable flask comprising flat stirring blades made of stainless steel (R1375 manufactured by IKA Corporation, blade diameter 70 mm) and a Three-one motor manufactured by SHINTO Scientific Co., Ltd. (BL600). The temperature was raised to 55° C. to 60° C., the filtrate was maintained at 250 rotations/minute for 15 minutes. Then, 2.25 g epichlorohydrin was added to the reaction mixture at a fixed temperature of 55 to 60° C., and the mixture was maintained at 55 to 60° C. for 3 hours. The reaction mixture was cooled to 25° C. to 35° C., and the product was isolated by filtration. The wet cake was further loosened with water (3×375 mL) at 25 to 50° C., washed for 45 minutes, filtered and dried at 50° C. in a ventilation drier to obtain crosslinked polyallylamine globules. A scanning electron microscopy image of Comparative Example 5 was shown in FIG. 7, and an optical microscope photograph of Comparative Example 5 was shown in FIG. 8. As is understood from FIG. 8, the particles of Comparative Example 5 contain having a distorted shape which is not circular and have a low circularity.

Comparative Example 6

Synthesis was performed based on Example 2 of Patent Literature 6.

That is, 22.8 g of a 40.0% by mass polyallylamine aqueous solution, 5.79 mL of 30% by mass hydrochloric acid and 6.10 g of sodium chloride were mixed in a 500-mL separable flask comprising flat stirring blades made of stainless steel (R1375 manufactured by IKA Corporation, blade diameter 70 mm) and a Three-one motor manufactured by SHINTO Scientific Co., Ltd. (BL600) to obtain a 32.3% by weight aqueous solution of polyallylamine hydrochloride. The obtained mixture was cooled to 5° C. Then, 120 mL of toluene and 0.57 g of Span 85 (sorbitan trioleate) were added. All of 1.8 mL of epichlorohydrin were added to the partially neutralized polyallylamine hydrochloride solution at once. This solution was immediately stirred at 1200 rotations/minute, resulting in dispersion in toluene. The mixture was heated to 60° C. and stirred for 3 hours. The toluene was removed by decantation. The formed crosslinked polyallylamine hydrochloride was suspended by stirring in 150 mL of deionized water for 45 minutes, washed 3 times and subsequently filtered. The crosslinked solid was rinsed once by stirring the crosslinked solid in 200 mL of isopropanol for 45 minutes and suspending the mixture, and subsequently filtered. The solid was vacuum-dried for 8 hours to obtain crosslinked polyallylamine globules. A scanning electron microscopy image of Comparative Example 6 was shown in FIG. 9, and an optical microscope photograph of Comparative Example 6 was shown in FIG. 10. As is understood from FIG. 10, the particles of Comparative Example 6 contain having a distorted shape and have a low circularity.

[Test Example 1] Serum Phosphorus Concentration Lowering Effect in Normal Rat

Sprague Dawley® (male, 6 weeks old, available from Charles River Laboratories Japan, Inc.) rats were purchased; two to four of them were accommodated in a breeding room at a temperature of 19 to 25° C. and a humidity of 30 to 70% with 12-hour lighting per day (7:00 AM to 7:00 PM); and they were fed with FR-2 solid feed (manufactured by Funabashi Farm Co., Ltd.) and water ad libitum. After 1-week quarantine and conditioning breeding, individuals having no abnormal appearance found were used for tests; then, the feed was switched from FR-2 solid feed to FR-2 powder feed (manufactured by Funabashi Farm Co., Ltd.); and conditioning for the powder feed was carried out for further 2 to 3 days.

Thereafter, a body weight was measured and blood was collected from the tail vain into a 400 μL-serum separator tube. The blood was centrifuged by a centrifuge (CF15RX1 manufactured by HITACHI) at 3000 rpm and 4° C. for 20 minutes; and a supernatant was used as a serum sample to measure a serum phosphorus concentration by phosphor C-test Wako (Wako Pure Chemical Industries, Ltd.). The rats were divided into groups using the serum phosphorus concentration and the body weight as indexes so as to equalize each group (N=6), and each of the following agents was mixed in FR-2 powder feed and administered to the respective groups.

Example 1-1-administered group; the crosslinked polyallylamine globules obtained in Example 1-1 were mixed at 1% by mass in the diet and administered.

Example 1-2-administered group; the crosslinked polyallylamine globules obtained in Example 1-2 were mixed at 1% by mass in the diet and administered.

Example 1-3-administered group; the crosslinked polyallylamine globules obtained in Example 1-3 were mixed at 1% by mass in the diet and administered.

Comparative Example 5-administered group; the crosslinked polyallylamine globules obtained in Comparative Example 5 were mixed at 1% by mass in the diet and administered.

Comparative Example 6-administered group; the crosslinked polyallylamine globules obtained in Comparative Example 6 were mixed at 1% by mass in the diet and administered.

Sevelamer hydrochloride-administered group; Sevelamer hydrochloride of Comparative Example 1 was mixed at 1% by mass in the diet and administered.

Double amount Sevelamer hydrochloride-administered group; Sevelamer hydrochloride of Comparative Example 2 was mixed at 2% by mass in the diet and administered.

Double amount Bixalomer-administered group; Bixalomer of Comparative Example 4 was mixed at 2% by mass in the diet and administered.

Control group; FR-2 powder feed containing none of agents was given.

Three days after the start of the agent-mixed diet administration, blood was collected from the tail vein to measure a serum phosphorus concentration and thereby, a serum phosphorus concentration lowering effect of an agent was evaluated. Regarding the serum phosphorus concentration, an average of individual values of each group with ±standard error was calculated and shown in Table 4.

TABLE 4

| Group type | Serum phosphorus concentration (mg/dL) |
|---|---|
| Control group | 7.9 ± 0.2 |
| Example 1-1-administered group | 5.7 ± 0.4 |
| Example 1-2-administered group | 6.0 ± 0.3 |
| Example 1-3-administered group | 5.9 ± 0.2 |
| Comparative Example 5-administered group | 8.4 ± 0.2 |
| Comparative Example 6-administered group | 8.1 ± 0.1 |
| Sevelamer hydrochloride-administered group | 7.2 ± 0.3 |
| Double amount Sevelamer hydrochloride-administered group | 5.8 ± 0.1 |
| Double amount Bixalomer-administered group | 6.4 ± 0.2 |

All of Example 1-1-administered group, Example 1-2-administered group, and Example 1-3-administered group showed a lower serum phosphorus concentration compared to Control group. That is, the above suggested that crosslinked polyallylamine globules obtained in all of Examples 1-1, 1-2 and 1-3 had a phosphorus adsorption effect.

In addition, all of Example 1-1-administered group, Example 1-2-administered group, and Example 1-3-administered group had a lower serum phosphorus concentration compared to Comparative Example 5-administered group, Comparative Example 6-treated group or Sevelamer hydrochloride-administered group. That is, the above suggested that crosslinked polyallylamine globules obtained in all of Examples 1-1, 1-2 and 1-3 had a stronger phosphorus adsorption effect compared to the crosslinked polyallylamine globules obtained in Comparative Example 5, the crosslinked polyallylamine globules obtained in Comparative Example 6 or Sevelamer hydrochloride.

Further, all of Example 1-1-administered group, Example 1-2-administered group, and Example 1-3-administered group showed an equivalent serum phosphorus concentration compared to Double amount Sevelamer hydrochloride-administered group or Double amount Bixalomer-administered group. That is, the above suggested that crosslinked polyallylamine globules obtained in all of Examples 1-1, 1-2 and 1-3 had a phosphorus adsorption effect equivalent to that of Double amount Sevelamer hydrochloride or Double amount Bixalomer.

[Test Example 2] Serum Phosphorus Concentration Lowering Effect in Adenine Nephropathy Model Rats Sprague Dawley® (male, 6 weeks old, available from Charles River Laboratories Japan, Inc.) rats were purchased; two to four of them were accommodated in a breeding room at a temperature of 19 to 25° C. and a humidity of 30 to 70%, with 12-hour lighting per day (7:00 AM to 7:00 PM); and they were fed with FR-2 solid feed (manufactured by Funabashi Farm Co., Ltd.) and water ad libitum. After 1-week quarantine and conditioning breeding, rats with no abnormal appearance were used for tests; a body weight of each rat was measured and an individual identification number was given to each rat; and the rats were divided into groups of two or three for one cage. At the same time, FR-2 solid feed was removed; and high phosphorus and high adenine content FR-2 powder feed (Oriental Yeast Co., Ltd.) was placed in an aluminum feeding bowl to conduct feeding for 2 weeks. Normal Control group (N=6) was fed with FR-2 powder feed (manufactured by Funabashi Farm Co., Ltd.). During that period, feed was supplemented appropriately at a frequency of 1 to 2 times per week. Cage exchange was conducted at a frequency of 2 to 3 times per week.

On the day after 2-week feeding, a body weight was measured and blood was collected from the tail vain into a 400 μL-serum separable tube. The collected blood was centrifuged by use of a centrifuge (CF15RX1, HITACHI) at 3000 rpm and 4° C. for 20 minutes; and a supernatant was used as a serum sample to measure a serum phosphorus concentration by phosphor C-test Wako (Wako Pure Chemical Industries, Ltd.). Further, the same serum sample was used for the measurement of blood urea nitrogen (BUN) and serum creatinine (CRNN) concentration by Hitachi 7010 Automatic Analyzer. It was confirmed that rats fed with high phosphorus and high adenine content FR-2 powder feed (hereinafter, referred to as disease rats) had increased serum phosphorus concentration, BUN and serum CRNN concentration compared to Normal Control group. Then, the serum phosphorus concentration, BUN, serum CRNN concentration and weight were used as indexes to make subgrouping so that values of the indexes were uniform among Control group and groups treated with respective agents (each group: N=8 to 9). For 2 weeks from the day after the blood collection and measurements, each of the following agents was mixed in high phosphorus and high adenine content FR-2 powder feed and administered to the respective groups. For Control group, cellulose (manufactured by Nacalai Tesque, Inc.) was mixed in high phosphorus and high adenine content FR-2 powder feed and administered. For Normal Control group, cellulose was mixed in FR-2 powder feed and administered. During that period, feed was supplemented at a frequency of 1 to 2 times per week. Cage exchange was conducted at a frequency of 2 to 3 times per week.

Example 1-1-administered group; crosslinked polyallylamine globules obtained in Example 1-1 were mixed at 2% by mass in the diet and administered to disease rats. Further, cellulose was mixed at 2% by mass in the diet, and, in total, the agents were mixed at 4% by mass in the diet and administered.

Example 2-administered group; crosslinked polyallylamine globules obtained in Example 2 were mixed at 2% by mass in the diet and administered to disease rats. Further, cellulose was mixed at 2% by mass in the diet, and, in total, the agents were mixed at 4% by mass in the diet and administered.

Example 3-administered group; crosslinked polyallylamine globules obtained in Example 3 were mixed at 2% by mass in the diet and administered to disease rats. Further, cellulose was mixed at 2% by mass in the diet, and, in total, the agents were mixed at 4% by mass in the diet and administered.

Example 4-administered group; crosslinked polyallylamine globules obtained in Example 4 were mixed at 2% by mass in the diet and administered to disease rats. Further, cellulose was mixed at 2% by mass in the diet, and, in total, the agents were mixed at 4% by mass in the diet and administered.

Bixalomer-administered group; Bixalomer of Comparative Example 3 was mixed at 2% by mass in the diet and administered to disease rats. Further, cellulose was mixed at 2% by mass in the diet, and, in total, the agents were mixed at 4% by mass in the diet and administered.

Double amount Bixalomer-administered group; Bixalomer of Comparative Example 4 was mixed at 4% by mass in the diet and administered to diseases rats.

Control group; cellulose was mixed at 4% by mass in the diet and administered to disease rats.

Normal Control group; cellulose was mixed at 4% by mass in the diet and administered to normal rats.

13 days after the start of the agent-mixed diet administration, blood was collected from the tail vain to measure a serum phosphorus concentration and thereby, a serum phosphorus concentration lowering effect of an agent was evaluated. Regarding the serum phosphorus concentration, an average of individual values of each group with ±standard error was calculated and shown in Table 5.

TABLE 5

| Group type | Serum phosphorus concentration (mg/dL) |
| --- | --- |
| Normal Control group | 7.4 ± 0.2 |
| Control group | 13.5 ± 0.5 |
| Example 1-1-administered group | 7.2 ± 0.3 |
| Example 2-administered group | 7.7 ± 0.3 |
| Example 3-administered group | 7.9 ± 0.5 |
| Example 4-administered group | 7.8 ± 0.4 |
| Bixalomer-administered group | 9.5 ± 0.8 |
| Double amount Bixalomer-administered group | 8.4 ± 0.3 |

In comparison with Normal Control group, Control group had a higher serum phosphorus concentration, and it was confirmed that hyperphosphatemia was appropriately initiated in disease rats of this test.

All of Example 1-1-administered group, Example 2-administered group, Example 3-administered group and Example 4-administered group showed a lower serum phosphorus concentration compared to Control group. That is, the above suggested that crosslinked polyallylamine globules obtained in all of Examples 1-1, 2, 3 and 4 had a phosphorus adsorption effect.

In addition, Example 1-1-administered group, Example 2-administered group, Example 3-administered group and Example 4-administered group had a lower serum phosphorus concentration compared to Bixalomer-administered group. That is, the above suggested that crosslinked polyallylamine globules obtained in all of Examples 1-1, 2, 3 and 4 had a stronger phosphorus adsorption effect compared to Bixalomer.

Further, Example 1-1-administered group, Example 2-administered group, Example 3-administered group and Example 4-administered group showed a serum phosphorus concentration equivalent to that of Double amount Bixalomer-administered group. That is, the above suggested that crosslinked polyallylamine globules obtained in all of Examples 1-1, 2, 3 and 4 had a serum phosphorus concentration equivalent to that of Double amount Bixalomer.

Further, the same tests as described above were carried out while each of the following agents was mixed in the diet and administered to the respective groups.

Example 1-1-administered group; crosslinked polyallylamine globules obtained in Example 1-1 were mixed at 2% by mass in the diet and administered to disease rats. Further, mass of cellulose was mixed at 2% by mass in the diet, and, in total, the agents were mixed at 4% by mass in the diet and administered.

Double amount Sevelamer hydrochloride-administered group; Sevelamer hydrochloride of Comparative Example 2 was mixed at 4% by mass in the diet and administered to disease rats.

Bixalomer-administered group; Bixalomer of Comparative Example 3 was mixed at 2% by mass in the diet and administered to disease rats. Further, cellulose was mixed at 2% by mass in the diet, and, in total, the agents were mixed at 4% by mass in the diet and administered.

Double amount Bixalomer-administered group; Bixalomer of Comparative Example 4 was mixed at 4% by mass in the diet and administered to disease rats.

Control group; cellulose was mixed at 4% by mass in the diet and administered to disease rats.

Normal Control group; cellulose was mixed at 4% by mass in the diet and administered to normal rats.

13 days after the start of the agent-mixed diet administration, blood was collected from the tail vain to measure a serum phosphorus concentration thereof and thereby, a serum phosphorus concentration lowering effect of an agent was evaluated. Regarding the serum phosphorus concentration, an average of individual values of each group with ±standard error was calculated and shown in Table 6.

TABLE 6

| Group type | Serum phosphorus concentration (mg/dL) |
| --- | --- |
| Normal Control group | 7.3 ± 0.1 |
| Control group | 11.8 ± 0.4 |
| Example 1-1-administered group | 8.0 ± 0.5 |
| Double amount Sevelamer hydrochloride-administered group | 8.2 ± 0.5 |
| Bixalomer-administered group | 9.6 ± 0.7 |
| Double amount Bixalomer-administered group | 9.0 ± 0.2 |

In comparison with Normal Control group, Control group had a higher serum phosphorus concentration, and it was confirmed that hyperphosphatemia was appropriately initiated in disease rats of this test.

Example 1-1-administered group showed a lower serum phosphorus concentration compared to Bixalomer-administered group. That is, the above suggested that crosslinked polyallylamine globules obtained in Example 1-1 had a stronger phosphorus adsorption effect compared to Bixalomer.

In addition, Example 1-1-administered group had a serum phosphorus concentration equivalent to those of Double amount Sevelamer hydrochloride-administered group and Double amount Bixalomer-administered group. That is, the above suggested that crosslinked polyallylamine globules obtained in Example 1-1 had a phosphorus adsorption effect equivalent to those of Double amount Sevelamer hydrochloride and Double amount Bixalomer.

From the above Test Examples 1 and 2, it was confirmed that crosslinked polyallylamine globules described in each Example had the same or better drug efficacy than Double amount Sevelamer hydrochloride or Double amount Bixalomer. From these tests, it is inferred that particles containing crosslinked polymer of the present invention have the same or better drug efficacy than Double amount Sevelamer hydrochloride or Double amount Bixalomer.

In the case of Sevelamer hydrochloride or Bixalomer, a large amount thereof has to be prescribed for patients with hyperphosphatemia; however, according to the present invention, the prescription volume can be reduced to a half or less for those patients. As a result, drug compliance arising from high doses is improved, and a good control of serum phosphorus concentration and a reduction of dosing stress are expected.

Example 11

Into a 1-L separable flask (cylindrical type with an inner diameter of 120 mm, Product No. 6-741-10 manufactured by AS ONE Corporation) having a Dean-Stark device and having a PTFE all-coated stirring bar (twister-type manufactured by Flonchemical Co., Ltd., blade diameter of 80 mm) as a stirring blade and a Three-one motor (BL600) manufactured by SHINTO Scientific Co., Ltd., 8.00 g of ethyl cellulose (Ethyl Cellulose 45 (about 49% ethoxy) manufactured by Wako Pure Chemical Corporation, weight average molecular weight: 125,000), 1.24 g of 1,6-dichlorohexane (manufactured by Tokyo Chemical Industry Co., Ltd.), 425.9 g of toluene and 47.3 g of ethanol were added and stirred at 40° C. at 230 rotations per minute for 1 hour, resulting in complete dissolution of ethyl cellulose. Thereafter, 162 g of a 15.0% by mass polyallylamine (PAA-15C manufactured by NITTOBO MEDICAL CO., LTD., amine value 17.5 mmol/g) aqueous solution was dropped over 1 hour. The above mixture was stirred at 40° C. at 200 rotations per minute for 60 minutes, so that a polyallylamine emulsion was obtained. Then, the bath temperature was increased to 120° C. and reflux was carried out for 20 hours, thereby removing 180 mL of water.

The temperature of a flask was cooled to room temperature and filtration was carried out. Then, particles obtained after being washed with ethanol were charged into a beaker, and stirred with 300 ml of water and 3 ml of 2N—NaOH aqueous solution for 1 hour. Thereafter, washing was carried out with 300 ml of water five times and then, washed with ethanol (300 mL, once); and the obtained particles were dried by a vacuum dryer at 70° C. for 20 hours, so that crosslinked polymer globules were obtained.

Example 12

Into a 500-ml separable flask (cylindrical flat bottom type manufactured by SIBATA; Product No. 005820-500) having a Dean-Stark device and having a flat stirring blade made of stainless (R1375 manufactured by IKA; blade diameter of 70 mm) and a Three-one motor (BL600) manufactured by SHINTO Scientific Co., Ltd., 3.32 g of ethyl cellulose (Ethyl Cellulose 45 (about 49% ethoxy) manufactured by Wako Pure Chemical Corporation, weight average molecular weight: 125,000), 0.92 g of 1,6-dichlorohexane (manufactured by Tokyo Chemical Industry Co., Ltd.), 237 g of toluene and 26.3 g of ethanol were charged and stirred at 40° C. at 200 rotations per minute for 1 hour, resulting in complete dissolution of ethyl cellulose. Thereafter, 90 g of a 15.0% by mass polyallylamine (PAA-15C manufactured by NITTOBO MEDICAL CO., LTD., amine value 17.5 mmol/g) aqueous solution was dropped over 1 hour. The above mixture was stirred at 40° C. at 200 rotations per minute for 60 minutes, so that a polyallylamine emulsion was obtained. Then, the bath temperature was increased to 120° C. and reflux was carried out for 20 hours, thereby removing 88 mL of water. The temperature of a flask was cooled to room temperature and filtration was carried out. Then, particles obtained after being washed with ethanol were charged into a beaker, and stirred with 200 ml of water and 2 ml of 2N—NaOH aqueous solution for 1 hour. Thereafter, washing was carried out with 200 ml of water five times and then, washed with ethanol (200 mL, once); and the obtained particles were dried by a vacuum dryer at 70° C. for 20 hours, so that crosslinked polymer globules were obtained.

Example 13

Crosslinked polyallylamine globules were obtained in the same way as in Example 12 except that the number of stirring rotations was changed from 200 to 250 rotations per minute and the mass of ethyl cellulose was changed from 3.32 g to 5.59 g.

Example 14

Crosslinked polyallylamine globules were obtained in the same way as in Example 11 except that the emulsifying temperature was changed from 40° C. to 22° C., the number of stirring rotations was changed from 200 to 350 rotations per minute, and the mass of ethyl cellulose was changed from 3.32 g to 5.59 g.

Example 15

Crosslinked polyallylamine globules were obtained in the same way as in Example 11 except that the number of stirring rotations was changed from 230 to 170 rotations per minute.

Example 16

Crosslinked polyallylamine globules were obtained in the same way as in Example 11 except that the number of stirring rotations was changed from 230 to 290 rotations per minute.

Example 17

Crosslinked polyallylamine globules were obtained in the same way as in Example 12 except that: 90 g of a 15.0% by mass polyallylamine aqueous solution was changed to 90 g of a 22.0% by mass polyallylamine (PAA-15C manufactured by NITTOBO MEDICAL CO., LTD., amine value 17.5 mmol/g, concentrated from 15 wt %) aqueous solution; the mass of dichlorohexane was changed to 1.01 g; and the mass of ethyl cellulose was changed from 3.32 g to 6.57 g.

Example 18

Crosslinked polyallylamine globules were obtained in the same way as in Example 12 except that: 90 g of a 15.0% by mass polyallylamine (PAA-15C manufactured by NITTOBO MEDICAL CO., LTD., average molecular weight 15000) aqueous solution was changed to 90 g of a 15.0% by mass polyallylamine (PAA-8 manufactured by NITTOBO MEDICAL CO., LTD., average molecular weight 8000) aqueous solution; the mass of dichlorohexane was changed from 0.92 g to 1.00 g; and the mass of ethyl cellulose was changed from 3.32 g to 4.45 g.

Production conditions and evaluation results for the above Examples are shown in the following tables. In the tables, the molecular weight represents a weight average molecular weight.

TABLE 7

| | Composition of first solution | Viscosity of first solution (mPa · S) | Solvent of second solution | Emulsifier | Viscosity of second solution (mPa · s) | Viscosity ratio (first solution/second solution) | Rotation number (rotations/minute) |
|---|---|---|---|---|---|---|---|
| Example 11 | 15% by mass polyallylamine (molecular weight 15000) aqueous solution | 21 | Toluene/ethanol = 90/10 | Ethyl cellulose (1.69% by mass) | 3.24 | 6.48 | 230 |

TABLE 7-continued

|  | Composition of first solution | Viscosity of first solution (mPa·S) | Solvent of second solution | Emulsifier | Viscosity of second solution (mPa·s) | Viscosity ratio (first solution/second solution) | Rotation number (rotations/ minute) |
|---|---|---|---|---|---|---|---|
| Example 12 | 15% by mass polyallylamine (molecular weight 15000) aqueous solution | 21 | Toluene/ethanol = 90/10 | Ethyl cellulose (1.26% by mass) | 2.1 | 10.0 | 200 |
| Example 13 | 15% by mass polyallylamine (molecular weight 15000) aqueous solution | 21 | Toluene/ethanol = 90/10 | Ethyl cellulose (2.12% by mass) | 4.73 | 4.44 | 250 |
| Example 14 | 15% by mass polyallylamine (molecular weight 15000) aqueous solution | 21 | Toluene/ethanol = 90/10 | Ethyl cellulose (0.9% by mass) | 1.42 | 14.79 | 350 |
| Example 15 | 15% by mass polyallylamine (molecular weight 15000) aqueous solution | 21 | Toluene/ethanol = 90/10 | Ethyl cellulose (1.69% by mass) | 3.24 | 6.48 | 170 |
| Example 16 | 15% by mass polyallylamine (molecular weight 15000) aqueous solution | 21 | Toluene/ethanol = 90/10 | Ethyl cellulose (1.69% by mass) | 3.24 | 6.48 | 290 |
| Example 17 | 22% by mass polyallylamine (molecular weight 15000) aqueous solution | 52.4 | Toluene/ethanol = 90/10 | Ethyl cellulose (2.5% by mass) | 6.57 | 7.98 | 200 |
| Example 18 | 15% by mass polyallylamine (molecular weight 8000) aqueous solution | 11.8 | Toluene/ethanol = 90/10 | Ethyl cellulose (1.69% by mass) | 3.24 | 3.64 | 200 |

TABLE 8

|  | Polymer | Crosslinking agent | Circularity | Used amount of crosslinking agent (% by mass) | Swelling rate (mL/g) | Average particle diameter (μm) | CV value |
|---|---|---|---|---|---|---|---|
| Example 11 | Polyallylamine | Dichlorohexane | 0.94 | 2.7 | 13.6 | 47 | 35 |
| Example 12 | Polyallylamine | Dichlorohexane | 0.93 | 3.7 | 10.7 | 72 | 76 |
| Example 13 | Polyallylamine | Dichlorohexane | 0.92 | 3.7 | 10.8 | 40 | 49 |
| Example 14 | Polyallylamine | Dichlorohexane | 0.92 | 2.7 | 12.5 | 20 | 32 |
| Example 15 | Polyallylamine | Dichlorohexane | 0.92 | 2.7 | 14.2 | 51 | 50 |
| Example 16 | Polyallylamine | Dichlorohexane | 0.92 | 2.7 | 13 | 48 | 67 |
| Example 17 | Polyallylamine | Dichlorohexane | 0.9 | 2.7 | 11.1 | 79 | 77 |
| Example 18 | Polyallylamine | Dichlorohexane | 0.9 | 4.0 | 11.0 | 67 | 63 |

In the table, the amount of crosslinking agent (% by mass) used is a calculated ratio of the mass of a crosslinking site of a crosslinking agent excluding a leaving group relative to the mass of the entire of a crosslinking body.

Example 19

Crosslinked polyallylamine globules were obtained in the same way as in Example 11 except that: the mass of ethyl cellulose was changed from 8.00 g to 3.79 g; the mass of dichlorohexane was changed from 1.24 g to 1.65 g; and the number of stirring rotations at the time of emulsifying was changed from 230 to 350 rotations per minute.

Example 20

Crosslinked polyallylamine globules were obtained in the same way as in Example 11 except that: the mass of ethyl cellulose was changed from 8.00 g to 3.79 g; the mass of dichlorohexane was changed from 1.24 g to 1.06 g; and the number of stirring rotations at the time of emulsifying was changed from 230 to 350 rotations per minute.

Example 21

Crosslinked polyallylamine globules were obtained in the same way as in Example 11 except that the mass of dichlorohexane was changed from 1.24 g to 1.65 g and the number of stirring rotations at the time of emulsifying was changed from 230 to 500 rotations per minute.

Example 22

Crosslinked polyallylamine globules were obtained in the same way as in Example 11 except that the mass of dichlorohexane was changed from 1.24 g to 1.06 g and the number of stirring rotations at the time of emulsifying was changed from 230 to 500 rotations per minute.

TABLE 9

| | Composition of first solution | Viscosity of first solution (mPa · s) | Solvent of second solution | Emulsifier | Viscosity of second solution (mPa · s) | Viscosity ratio (first solution/ second solution) | Rotation number (rotations/ minute) |
|---|---|---|---|---|---|---|---|
| Example 19 | 15% by mass polyallylamine (molecular weight 15000) aqueous solution | 21 | Toluene/ethanol = 90/10 | Ethyl cellulose (0.8% by mass) | 1.30 | 16.2 | 350 |
| Example 20 | 15% by mass polyallylamine (molecular weight 15000) aqueous solution | 21 | Toluene/ethanol = 90/10 | Ethyl cellulose (0.8% by mass) | 1.30 | 16.2 | 350 |
| Example 21 | 15% by mass polyallylamine (molecular weight 15000) aqueous solution | 21 | Toluene/ethanol = 90/10 | Ethyl cellulose (1.69% by mass) | 3.24 | 6.48 | 500 |
| Example 22 | 15% by mass polyallylamine (molecular weight 15000) aqueous solution | 21 | Toluene/ethanol = 90/10 | Ethyl cellulose (1.69% by mass) | 3.24 | 6.48 | 500 |

TABLE 10

| | Polymer | Crosslinking agent | Amount of crosslinking agent used (% by mass) | Swelling rate (mL/g) | Average particle diameter (μm) |
|---|---|---|---|---|---|
| Example 19 | Polyallylamine | Dichlorohexane | 3.6 | 8.1 | 80 |
| Example 20 | Polyallylamine | Dichlorohexane | 2.3 | 12.8 | 88 |
| Example 21 | Polyallylamine | Dichlorohexane | 3.6 | 10.3 | 31 |
| Example 22 | Polyallylamine | Dichlorohexane | 2.3 | 13.1 | 38 |

In the table, the amount of crosslinking agent used (% by mass) is a calculated ratio of the mass of a crosslinking site of a crosslinking agent excluding a leaving group relative to the mass of the entire of a crosslinking body.

TABLE 11

| | Amine value (mmol/g) | Phosphate adsorption capacity (mmol/g) | Restrained part (Hard) | | | Semi-restrained part (Mid) | | | Non-restrained part (Soft) | | |
|---|---|---|---|---|---|---|---|---|---|---|---|
| | | | $T_{2,1}$ (ms) | $A_1$ | Ratio | $T_{2,2}$ (ms) | $A_2$ | Ratio | $T_{2,3}$ (ms) | $A_3$ | Ratio |
| Example 11 | — | 8.5 | 0.100 | 0.36 | 54% | 1.146 | 0.30 | 45% | 1750 | 0.01 | 1% |
| Example 19 | 15.8 | 8.1 | 0.100 | 0.40 | 60% | 1.288 | 0.26 | 39% | 101.5 | 0.00 | 1% |
| Example 20 | 16.0 | 8.3 | 0.111 | 0.28 | 47% | 1.384 | 0.32 | 53% | — | 0.00 | 0% |
| Example 21 | 15.8 | 8.2 | 0.111 | 0.40 | 59% | 1.270 | 0.28 | 41% | — | 0.00 | 0% |
| Example 22 | 16.2 | 8.3 | 0.131 | 0.32 | 47% | 1.367 | 0.32 | 47% | 2.450 | 0.05 | 7% |

The invention claimed is:

1. A method for treating hyperphosphatemia, which comprises administering, to a subject, a particle comprising a crosslinked polymer having at least a repeating unit A represented by the following formula (1-1) or (1-2) and a repeating unit B represented by the following formula (2-1) or (2-2):

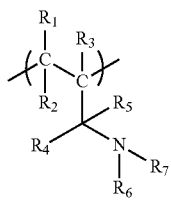
(1-1)

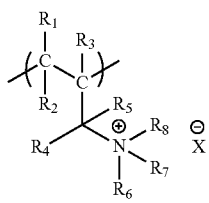
(1-2)

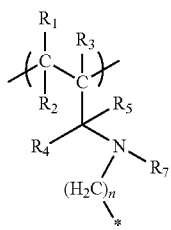
(2-1)

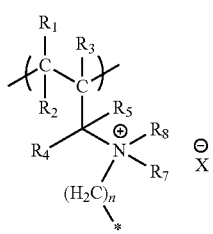
(2-2)

wherein:

$R_1$, $R_2$, $R_3$, $R_4$ and $R_5$ each independently represent a hydrogen atom, a halogen atom, or an alkyl group having 1 to 20 carbon atoms;

$R_6$, $R_7$ and $R_8$ each independently represent a hydrogen atom, an alkyl group having 1 to 20 carbon atoms, an aminoalkyl group having 1 to 20 carbon atoms or a salt thereof, an alkylaminoalkyl group having 2 to 20 carbon atoms or a salt thereof, a dialkylaminoalkyl group having 3 to 20 carbon atoms or a salt thereof, a trialkylammoniumalkyl group having 4 to 20 carbon atoms, an alkylcarbonyl group having 1 to 20 carbon atoms, a carboxyalkyl group having 1 to 20 carbon atoms, or a hydroxyalkyl group having 1 to 20 carbon atoms;

$X^-$ is a negatively charged counter ion, n represents 6, symbol * denotes a bond with a nitrogen atom on the side chain of the repeating unit A, and in this case, at least one of $R_6$, $R_7$ and $R_8$ is a bond.

2. The method according to claim 1,
wherein:
$R_1$, $R_2$, $R_3$, $R_4$ and $R_5$ each independently represent a hydrogen atom or an alkyl group having 1 to 20 carbon atoms; and
$R_6$, $R_7$ and $R_8$ each independently represent a hydrogen atom or an alkyl group having 1 to 20 carbon atoms.

3. The method according to claim 1,
wherein:
$R_1$, $R_2$, $R_3$, $R_4$ and $R_5$ represent a hydrogen atom; and
$R_6$, $R_7$ and $R_8$ represent a hydrogen atom.

4. The method according to claim 1, wherein the particle has an average particle diameter of 20 to 150 μm,
wherein the average particle diameter is calculated as a volume average particle diameter by converting an area of 1000 or more imaged particles dispersed in water in an optical microscope photograph to diameters and using the diameters.

5. The method according to claim 1, wherein the particle has a swelling rate of 8 to 20 mL/g,
wherein the swelling rate is calculated by dividing, by a mass of the particle before swelling, a volume of the swollen particle which is obtainable by repeating shaking and 1-hour or longer still standing 20 or more times in an aqueous solution containing 2.2% by mass of sodium 2-morpholinoethanesulfonate and 0.5% by mass of sodium chloride and having a pH of 6.3 at 20° C.

6. The method according to claim 1, wherein the particle is a globule.

7. The method according to claim 1, wherein the content of the repeating unit A in all the crosslinked polymers is 90 to 99% by mole, and the content of the repeating unit B in all the crosslinked polymers is 1 to 10% by mole.

8. The method according to claim 1, wherein when a free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the particle has a proportion of a semi-restrained part of 25 to 70%.

9. The method according to claim 1, wherein when a free induction attenuation signal obtained in pulse NMR is subjected to waveform separation by subtracting components in the descending order in terms of spin-spin relaxation time T2 using a least-square method, whereby the particle is divided into three components: a non-restrained part, a semi-restrained part and a restrained part in the descending order in terms of spin-spin relaxation time, the particle has a proportion of the restrained part of 30 to 70%.

10. The method according to claim 1 wherein a phosphate adsorption capacity of the particle is 6.0 to 10.0 mmol/g,
wherein the phosphate adsorption capacity is calculated by: when 30 mg of particles is mixed and stirred at 37° C. for 1 hour in 20 mL of aqueous solution containing 2.2% by mass of sodium morpholinoethanesulfonate, 0.47% by mass of sodium chloride and 0.24% by mass of phosphate and having a pH of 6.4, quantifying phosphate concentrations in a supernatant before and after mixing by ICP emission spectrochemical analysis; dividing a decrease thereof by a mass of the particles; and correcting by use of a loss on drying.

11. The method according to claim 1 wherein an amine value of the particle is 11.0 to 17.5 mmol/g, wherein the amine value is calculated by: treating particles dispersed in ultrapure water with 5 N hydrochloric acid; quantifying an amino group by conducting neutralization titration with 0.1 N sodium hydroxide aqueous solution; dividing by a mass of the particles; and correcting by use of a loss on drying.

* * * * *